(12) United States Patent
Mori et al.

(10) Patent No.: US 11,168,159 B2
(45) Date of Patent: Nov. 9, 2021

(54) ZWITTERIONIC POLYMER, METHOD FOR PRODUCING SAME AND PROTEIN STABILIZER CONTAINING ZWITTERIONIC POLYMER

(71) Applicants: NATIONAL UNIVERSITY CORPORATION YAMAGATA UNIVERSITY, Kamagata (JP); NOF CORPORATION, Tokyo (JP)

(72) Inventors: Hideharu Mori, Yamagata (JP); Ryutaro Imamura, Ibaraki (JP)

(73) Assignees: NATIONAL UNIVERSITY CORPORATION YAMAGATA UNIVERSITY, Yamagata (JP); NOF CORPORATION, Tokyo (JP)

( * ) Notice: Subject to any disclaimer, the term of this patent is extended or adjusted under 35 U.S.C. 154(b) by 0 days.

(21) Appl. No.: 16/955,375

(22) PCT Filed: Dec. 26, 2018

(86) PCT No.: PCT/JP2018/047836
§ 371 (c)(1),
(2) Date: Jun. 18, 2020

(87) PCT Pub. No.: WO2019/131757
PCT Pub. Date: Jul. 4, 2019

(65) Prior Publication Data
US 2021/0017309 A1 Jan. 21, 2021

(30) Foreign Application Priority Data
Dec. 27, 2017 (JP) .............................. JP2017-250636

(51) Int. Cl.
*C08F 8/02* (2006.01)
*C08F 20/58* (2006.01)
*C07C 321/18* (2006.01)

(52) U.S. Cl.
CPC ............ *C08F 20/58* (2013.01); *C07C 321/18* (2013.01); *C08F 8/02* (2013.01)

(58) Field of Classification Search
CPC ............. C08F 8/02; C08F 28/04; C08F 20/58
See application file for complete search history.

(56) References Cited

U.S. PATENT DOCUMENTS

| | | | |
|---|---|---|---|
| 5,432,252 A | 7/1995 | Grosse-Bley et al. | |
| 5,645,883 A | 7/1997 | Russell et al. | |
| 5,739,237 A | 4/1998 | Russell et al. | |
| 2009/0306292 A1* | 12/2009 | Bendejacq | C08L 101/02 525/55 |
| 2015/0057433 A1* | 2/2015 | Deming | C07K 1/02 530/345 |

FOREIGN PATENT DOCUMENTS

| | | |
|---|---|---|
| CN | 103 435 746 B | 7/2015 |
| JP | H08-506030 A | 7/1996 |
| JP | H09-227629 | * 9/1997 |
| JP | H09-510963 A | 11/1997 |
| JP | 2009-528440 A | 8/2009 |
| WO | 2013/148727 A1 | 10/2013 |

OTHER PUBLICATIONS

Translation of JPH09-227629 (Year: 1997).*
Methenitis, Journal of Polymer Science: Part A: Polymer Chemstry, vol. 33, 2233-2239 (1995) (Year: 1995).*
Sanda, Polymer vol. 39, No. 22, pp. 5543-5547, 1998 (Year: 1998).*
T. Emrick and C.F. Santa Chalarca, "Reactive Polymer Zwitterions: Sulfonium Sulfonates", J. Polym. Chem., Sep. 22, 2016, pp. 55, 83-92 and CHALARCA.
R. Imamura et al., "Synthesis of Zwitterionic Polymers Containing a Tertiary Sulfonium Group for Protein Stabilization", Biomacromolecules, 2019, pp. 904-915.
International Search Report issued in International Patent Application No. PCT/JP2018/047836, dated Mar. 26, 2019.
International Preliminary Report on Patentability issued in International Patent Application No. PCT/JP2018/047836, dated Jun. 30, 2020, English translation.
Extended European Search Report issued in EPO Patent Application No. 18896409.2, dated Aug. 10, 2021.
Reid et al, "Selective Identification and Quantitative Analysis of Methionine Containing Peptides by Charge Derivatization and Tandem Mass Spectrometry", Journal of the American Society for Mass Spectrometry 2005, 16, pp. 1131-1150, published online May 31, 2005.
Zhang et al, "Zwitterionic gel encapsulation promotes protein stability, enhances pharmacokinetics, and reduces immunogenicity", Proceedings of the National Academy of Sciences, Sep. 29, 2015, vol. 112, No. 39, pp. 1246-12051.
Keefe et al, "Poly(zwitterionic)protein conjugate offer increased stability without sacrificing binding affinity or bioactivity", Nature Chemistry vol. 4, Jan. 2021, published online Dec. 11, 2011, pp. 59-63.

* cited by examiner

*Primary Examiner* — Robert C Boyle
(74) *Attorney, Agent, or Firm* — Greenblum & Bernstein P.L.C.

(57) ABSTRACT

Provided is a zwitterionic polymer that has a zwitterion that includes an effect of improving the stability of proteins. This zwitterionic polymer is a polymeric protein stabilizer that exhibits a protein stabilizing effect even at a small addition amount of addition, and at the same time has an antioxidant capability. Also provided is a method for producing this zwitterionic polymer. This problem is solved by a zwitterionic polymer containing a repeating unit represented by formula (1) and having a number-average molecular weight of 1,000 to 1,000,000. On formula (1), $R^1$ and $R^2$ are each independently selected from a hydrogen atom; linear, branched or cyclic alkyl groups having 1 to 6 carbons; aromatic groups having 6 to 20 carbons; or alkylene groups having 1 to 6 carbons and formed by linking $R^1$ to $R^2$. $R^3$ represents a hydrogen atom or a methyl group).

9 Claims, No Drawings

ZWITTERIONIC POLYMER, METHOD FOR PRODUCING SAME AND PROTEIN STABILIZER CONTAINING ZWITTERIONIC POLYMER

TECHNICAL FIELD

The present invention relates to a zwitterionic polymer, particularly to a zwitterionic polymer that enhances stability of a protein, a method for producing the same and a protein stabilizer.

BACKGROUND ART

Recently, physiologically active proteins such as antibodies, enzymes and cytokines are broadly employed in the fields of pharmaceutical products, clinical tests and diagnostic agents. When a protein or an antibody is administered as a pharmaceutical product or when an antibody is used to conduct a highly sensitive protein detection, the structure or the enzymatic activity of the protein needs to be maintained for a long period of time. Most of the proteins, however, can easily be denatured and deactivated due to stress such as temperature, freezing, pH, vibration and salt concentration as well as oxidative stress caused by hydroxyl radicals, singlet oxygen, nitric oxide or the like. Therefore, in order to store the proteins, addition of a protein stabilizer and an antioxidant is necessary.

As protein stabilizers, a wide variety of compounds ranging from low- to high-molecular compounds are used. As protein stabilizers, hydrophilic compounds are used, which enhance stability by hydrophilizing the surface of the protein. Examples of a low-molecular protein stabilizer include amino acids such as glycine and arginine, sugars such as sucrose and trehalose, and zwitterionic compounds such as non-detergent sulfobetaine (NDSB). In general, however, when a low-molecular stabilizer is used to stabilize a protein, it needs to be added at a concentration as high as several tens of weight percent, and thus such addition may cause a problem in the accuracy of biochemical measurements. Furthermore, since these low-molecular protein stabilizers have no function as an antioxidant, an antioxidant needs to be added separately.

Meanwhile, bovine serum albumin (BSA), polyethylene glycol (PEG) and the like are generally known to be used as high-molecular protein stabilizers. While these high-molecular protein stabilizers are capable of stabilizing a protein at a low concentration of 0.01 to several weight percent, BSA is a bovine-derived raw material and thus there is a concern about bovine spongiform encephalopathy (BSE) infection if it is to be added to a pharmaceutical product. Moreover, since these high-molecular protein stabilizers do not serve as an antioxidant, an antioxidant needs to be added separately.

Dimethylsulfoniopropionate (DMSP) is known as a low-molecular compound that serves both as a protein stabilizer and an antioxidant. DMSP is a compound found in marine phytoplankton, and is a zwitterionic compound that has a tertiary sulfonium group as the cationic moiety and a carboxyl group as the anionic moiety. Since, however, it is a low-molecular compound, it needs to be added at a high concentration for stabilizing the protein and thus may cause a problem in accuracy of biochemical measurements.

As a zwitterionic polymer having a similar structure to this DMSP, a non-patent reference (Todd Emrick, J. polym. Sci., Part A, 2017, 55, pp. 83-92) discloses a zwitterionic polymer represented by Formula (5) having a tertiary sulfonium group as the cationic moiety and sulfonic acid as the anionic moiety. This polymer is described to have an upper critical solution temperature (UCST) and does not dissolve in water at a temperature generally employed for treating proteins (4-25'C). Hence, this polymer cannot be used as a protein stabilizer.

[Chemical formula 1]

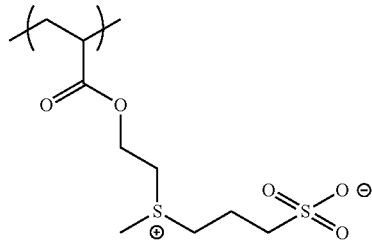

(5)

In addition, a patent reference (WO2013-148727A1) discloses a zwitterionic polymer represented by Formula (6) having a tertiary sulfonium group as the cationic moiety and a carboxyl group as the anionic moiety. If, however, the polymer described in this patent reference is to be used as a protein stabilizer for a pharmaceutical product or a diagnostic agent, chloroacetic acid or the like that is reactive with the substituent on the surface of the protein may be liberated due to degradation of the side chain of the polymer.

Moreover, even if it is used for stabilizing a degrading enzyme such as protease, it has a risk of being degraded and not exhibiting the protein stabilizing effect since the main chain includes a peptide bond. In addition, if it is used for stabilizing an antibody, it has a risk of being incorrectly recognized by the antibody and lowering the activity of the antibody itself.

[Chemical formula 2]

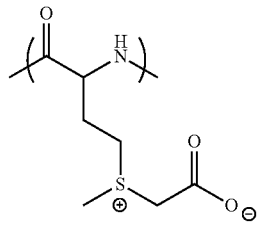

(6)

SUMMARY OF INVENTION

Technical Problem

Accordingly, a high-molecular protein stabilizer which has a zwitterion effective in enhancing stability of a protein, which is effective in stabilizing the protein in a small amount, and which, at the same time, has an antioxidant property, was not known until now.

The objective of the present invention is to provide a zwitterionic polymer which has a zwitterion effective in enhancing stability of a protein, which is effective in stabilizing the protein in a small amount and which, at the same time, has an antioxidant property, to provide a high-molecular protein stabilizer containing such a zwitterionic polymer, and to provide a method for producing said zwitterionic polymer.

Solution to Problem

The present inventors have gone through intensive investigation in order to achieve the above-described objective, and as a result of which they found that a zwitterionic polymer which has a zwitterion effective in enhancing stability of a protein, which is effective in stabilizing the protein in a small amount and which, at the same time, has an antioxidant property, as well as a high-molecular protein stabilizer containing such a zwitterionic polymer can solve the above-described problems.

Thus, the present invention provides [1]-[6] below.

[1] A zwitterionic polymer comprising a repeating unit represented by Formula (1) below and having a number-average molecular weight of 1,000-1,000,000,

[Chemical formula 3]

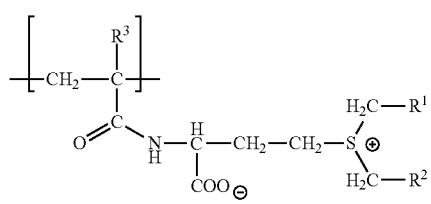

(1)

(in Formula (1), $R^1$ and $R^2$ each independently represent a hydrogen atom, a linear, branched or cyclic C1-C6 alkyl group, a C6-C20 aromatic group or a C1-C6 alkylene group in which $R^1$ and $R^2$ are linked to each other, and $R^3$ represents a hydrogen atom or a methyl group).

[2] The zwitterionic polymer according to [1] above, wherein $R^1$ and $R^2$ in Formula (1) above are both hydrogen atoms.

[3] The zwitterionic polymer according to [1] above, further comprising a structural unit derived from (meth)acrylate ester, wherein the ratio of the mole number x of the repeating unit represented by Formula (1) above and the mole number y of the structural unit derived from (meth)acrylate ester is in a range of x:y=10:90-95:5.

[4] A method for producing the zwitterionic polymer represented by Formula (1) above, the method comprising [Step A] and [Step B] below in this order:

[Step A]
radically polymerizing a sulfide acrylamide monomer represented by Formula (2) below;

[Chemical formula 4]

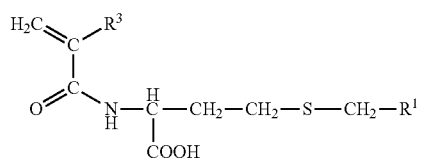

(2)

(wherein, $R^1$ represents a hydrogen atom, a linear, branched or cyclic C1-C6 alkyl group or a C6-C20 aromatic group, and $R^3$ represents a hydrogen atom or a methyl group); and

[Step B]
allowing the polymer obtained in [Step A] above to react with a sulfide-reactive compound represented by Formula (3) below,

[Chemical formula 5]

$$X—CH_2—R^2 \quad (3)$$

(wherein, X represents a chlorine atom, a bromine atom, an iodine atom, a mesyl group (methanesulfonyl group), a tosyl group (p-toluenesulfonyl group) or a trifluoromethanesulfonyl group, and $R^2$ represents a hydrogen atom, a linear, branched or cyclic C1-C6 alkyl group or a C6-C20 aromatic group).

[5] A method for producing the zwitterionic polymer represented by Formula (1) above, comprising a step of radically polymerizing a zwitterionic monomer represented by Formula (4) below in an aqueous solvent at 60° C. or lower,

[Chemical formula 6]

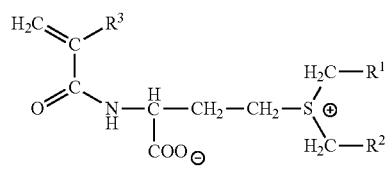

(4)

(wherein, $R^1$ and $R^2$ each independently represent a hydrogen atom, a linear, branched or cyclic C1-C6 alkyl group, a C6-C20 aromatic group or a C1-C6 alkylene group in which $R^1$ and $R^2$ are linked to each other, and $R^3$ represents a hydrogen atom or a methyl group).

[6] A zwitterionic monomer represented by Formula (4) above, which is an intermediate of the zwitterionic polymer represented by Formula (1) above.

[7] A protein stabilizer comprising the zwitterionic polymer represented by Formula (1) above.

Advantageous Effects of the Invention

The present invention can provide a high-molecular protein stabilizer which has a zwitterion effective in enhancing stability of a protein, which is effective in stabilizing the protein in a small amount and which, at the same time, has an antioxidant property, and a method for producing the same.

DESCRIPTION OF EMBODIMENT

Hereinafter, preferred embodiments of the present invention will be described in detail.

<Zwitterionic Polymer>

A zwitterionic polymer of the present invention refers to a zwitterionic polymer containing a repeating unit represented by Formula (1), which has a tertiary sulfonium group and a carboxyl group as side chains. The tertiary sulfonium group is a cationic substituent in which three carbon atoms are each attached to a sulfur atom via a single bond.

[Chemical formula 7]

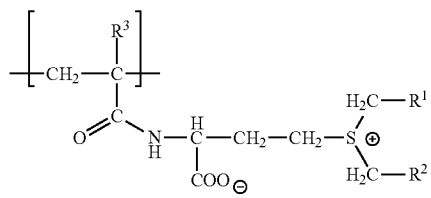

(1)

In Formula (1), $R^1$ and $R^2$ are each independently a substituent selected from, but not limited to, a hydrogen atom, a linear, branched or cyclic C1-C6 alkyl group, a C6-C20 aromatic group or a C1-C6 alkylene group in which $R^1$ and $R^2$ are linked to each other.

Examples of the linear alkyl group include a methyl group, an ethyl group, a propyl group, a n-butyl group, a pentyl group and a hexyl group; examples of the branched alkyl group include an isopropyl group and a 2-butyl group; and examples of the cyclic alkyl group include a cyclopentyl group and a cyclohexyl group. The carbon number of the alkyl group is preferably 1-4 and more preferably 1-3.

Examples of the C6-C20 aromatic group include a phenyl group, a p-nitrophenyl group, a bromophenyl group, phenylboronic acid, a hydroxyphenyl group, a dihydroxyphenyl group and a trihydroxyphenyl group. The carbon number of the aromatic group is preferably 6-12 and more preferably 6-10.

A C1-C6 alkylene group in which $R^1$ and $R^2$ are linked to each other is, for example, an alkylene group having a substituent represented by Formula (7) below. From the viewpoint of using the polymer of Formula (1) as a protein stabilizer, $R^1$ and $R^2$ are preferably a hydrogen atom, a methyl group, an ethyl group or a propyl group in order to enhance affinity of the polymer for water.

[Chemical Formula 8]

(7)

(In Formula (7), m represents an integer of 1 to 6, preferably 2-6 and more preferably an integer of 2-4).

In Formula (1) above, $R^3$ represents a hydrogen atom or a methyl group.

Examples of the zwitterionic polymer containing the repeating unit represented by Formula (1) above include a zwitterionic polymer in which $R^1$ and $R^2$ are both hydrogen atoms and $R^3$ is a hydrogen atom, a zwitterionic polymer in which $R^1$ is a propyl group, $R^2$ is a hydrogen atom and $R^3$ is a hydrogen atom, and a zwitterionic polymer in which $R^1$ is a benzyl group, $R^2$ is a hydrogen atom and $R^3$ is a hydrogen atom. For the sake of facilitating the synthesis, it is preferably a zwitterionic polymer in which $R^1$ and $R^2$ are both hydrogen atoms and $R^3$ is a hydrogen atom.

The zwitterionic polymer containing the repeating unit represented by Formula (1) may not only be formed of a single monomer but may also be a copolymer formed with other monomer. Specifically; the zwitterionic polymer may be composed of a plurality of types of monomers represented by Formula (1), or may include other monomer (comonomer) different from the monomer represented by Formula (1). Moreover, the zwitterionic polymer may be, for example, a random copolymer of two or more types of monomers.

The above-mentioned other monomer can appropriately be selected in accordance with the application, where examples thereof include: various (meth)acrylate esters such as diethylaminoethyl (meth)acrylate, polyethylene glycol mono(meth)acrylate, glycerol (meth)acrylate, (meth)acryloyloxy ethyl phosphate, (meth)acryloyloxy ethyl phosphorylcholine, N-methyl carboxybetaine (meth)acrylate, N-methyl sulfobetaine (meth)acrylate, methyl (meth)acrylate, ethyl (meth)acrylate, propyl (meth)acrylate, butyl (meth)acrylate, pentyl (meth)acrylate, hexyl (meth)acrylate, stearyl (meth)acrylate, glycidyl (meth)acrylate, dimethylamino ethyl (meth)acrylate, 2-hydroxyethyl methacrylate and methoxyethyl (meth)acrylate; various vinyl ethers such as methyl vinyl ether; as well as various radically-polymerizable monomers such as acrylamide, N,N'-dimethylacrylamide, N-isopropyl (meth)acrylamide, (meth)acrylic acid, allyl alcohol, acrylonitrile, acrolein, vinyl acetate, sodium vinylsulfonate, styrene, chlorostyrene, vinylphenol, vinyl cinnamate, vinyl chloride, vinyl bromide, butadiene, vinylene carbonate, itaconic acid, itaconic acid ester, fumaric acid, fumaric acid ester, maleic acid and maleic acid ester. If the zwitterionic polymer containing the repeating unit represented by Formula (1) above is to be used as a protein stabilizer, other monomer is preferably N,N'-dimethylacrylamide or (meth)acrylate ester such as butyl (meth)acrylate or polyethylene glycol mono(meth)acrylate in view of the balance considering solubility in a solvent. Furthermore, while the amount of other monomer to be blended is arbitrary and can appropriately be selected, in order to bring out the performance of the zwitterionic polymer containing the repeating unit represented by Formula (1), the content of other monomer to be blended is preferably 90 mol % or less and more preferably 70 mol % or less.

Moreover, the zwitterionic polymer containing the repeating unit represented by Formula (1) above may be a block copolymer formed with other monomer. The type of other monomer is the same as that for the random copolymerization, and if the zwitterionic polymer containing the repeating unit represented by Formula (1) is to be used as a protein stabilizer, other monomer is preferably butyl (meth)acrylate, or polyethylene glycol mono(meth)acrylate considering solubility in a solvent. Furthermore, while the amount of other monomer to be blended is arbitrary and can appropriately be selected, in order to bring out the performance of the zwitterionic polymer containing the repeating unit represented by Formula (1) above, the content of other monomer to be blended is preferably 90 mol % or less and more preferably 70 mol % or less.

The range of ratio x:y, i.e., the mole number x of the repeating unit represented by Formula (1) above (zwitterionic repeating unit) to the mole number y of a repeating unit originating from other monomer, in the zwitterionic polymer is, for example, x:y=10:90-95:5, preferably 20:80-92:8, more preferably 30:70-90:10 and still more preferably 32:68-82:14.

While the molecular weight of the zwitterionic polymer containing the zwitterionic repeating unit represented by Formula (1) above may suitably be determined by adjusting the polymerization conditions or the like to bring out the required performance, it is generally a number-average molecular weight of about 1,000-1,000,000, and if the polymer is to be used as a protein stabilizer, it is preferably a number-average molecular weight of 2,000-100,000, more preferably 3,000-50,000 and still more preferably 4,000-40,000 considering solubility in water.

<Method for Producing Zwitterionic Polymer>

A zwitterionic polymer of the present invention having a tertiary sulfonium group and a carboxyl group as the side chains can be produced by a production method which comprises at least [Step A] and [Step B] below in this order.

[Step A]

A step of radically polymerizing a sulfide (meth)acrylamide monomer represented by Formula (2) below to obtain a sulfide polymer as an intermediate.

[Chemical formula 9]

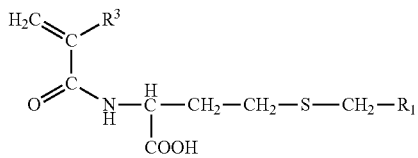

(2)

in Formula (2) above, $R^1$ is not particularly limited but can likely be defined as $R^1$ in Formula (1).

Specifically, in Formula (2), $R^1$ is selected from a hydrogen atom, a linear, branched or cyclic C1-C6 alkyl group or a C6-C20 aromatic group. Examples of the linear alkyl group include a methyl group, an ethyl group, a propyl group, a n-butyl group, a pentyl group and a hexyl group; examples of the branched alkyl group include an isopropyl group and a 2-butyl group; and examples of the cyclic alkyl group include a cyclopentyl group and a cyclohexyl group. The carbon number of the alkyl group is preferably 1-4 and more preferably 1-3.

Examples of the aromatic group include a phenyl group, a p-nitrophenyl group, a bromophenyl group, phenylboronic acid, a hydroxyphenyl group, a dihydroxyphenyl group and a trihydroxyphenyl group. The carbon number of the aromatic group is preferably 6-12 and more preferably 6-10.

From the viewpoint of using the polymer as a protein stabilizer, $R^1$ is preferably a hydrogen atom, a methyl group, an ethyl group or a propyl group in order to enhance affinity of the polymer for water.

In Formula (2) above, $R^3$ represents a hydrogen atom or a methyl group.

Examples of the sulfide monomer represented by Formula (2) above include a sulfide monomer in which $R^1$ is a hydrogen atom and $R^3$ is a hydrogen atom, a sulfide monomer in which $R^1$ is a propyl group and $R^3$ is a hydrogen atom, and a sulfide monomer in which $R^1$ is a benzyl group and $R^3$ is a hydrogen atom. For the sake of facilitating the synthesis, it is preferably a sulfide monomer in which $R^1$ is a hydrogen atom and $R^3$ is a hydrogen atom.

Among the sulfide monomers represented by Formula (2) above, sulfide monomers in which $R^1$ is a hydrogen atom are preferably obtained by performing (meth)acrylation of methionine using (meth)acryloyl chloride described in a non-patent reference, J. Morcellet., Makromol. Chem., 1981, 182, 949, for the sake of facilitating the synthesis. Moreover, sulfide monomers in which $R^1$ is a linear, branched or cyclic C1-C6 alkyl group or an aromatic group can be obtained by reacting the corresponding alkyl halide or aromatic halide with cysteine and subjecting the resultant to (meth)acrylation.

While the molecular weight of the sulfide polymer obtained by radically polymerizing, the sulfide monomer represented by Formula (2) above is not particularly limited and may suitably be determined by adjusting the polymerization conditions to bring out the required performance as a zwitterionic polymer after the subsequent [Step B], it is generally a number-average molecular weight of about 1,000-1,000,000, and if the sulfide polymer is to be used as a protein stabilizer, it is preferably a number-average molecular weight of 2,000-100,000. The number-average molecular weight is more preferably 3,000-50,000 and still more preferably 4,000-40,000.

The sulfide monomer represented by Formula (2) above may be obtained via polymerization solely, i.e., only one or two or more types, of sulfide monomers of Formula (2), or via polymerization of a mixture with other monomer (comonomer) that is polymerizable with the sulfide monomer represented by Formula (2) above. Other monomer can appropriately be selected in accordance with the application, where examples thereof include: various (meth)acrylate esters such as diethylaminoethyl (meth)acrylate, polyethylene glycol mono(meth)acrylate, glycerol (meth)acrylate, (meth)acryloyloxy ethyl phosphate, (meth)acryloyloxy ethyl phosphorylcholine, N-methyl carboxybetaine (meth)acrylate, N-methyl sulfobetaine (meth)acrylate, methyl (meth)acrylate, ethyl (meth)acrylate, propyl (meth)acrylate, butyl (meth)acrylate, pentyl (meth)acrylate, hexyl (meth)acrylate, stearyl (meth)acrylate, glycidyl (meth)acrylate, dimethylamino ethyl (meth)acrylate, 2-hydroxyethyl methacrylate and 2-methoxyethyl (meth)acrylate; various vinyl ethers such as methyl vinyl ether; as well as various radically-polymerizable monomers such as acrylamide, N,N'-dimethylacrylamide, N-isopropyl (meth)acrylamide, (meth)acrylic acid, allyl alcohol, acrylonitrile, acrolein, vinyl acetate, sodium vinylsulfonate, styrene, chlorostyrene, vinylphenol, vinyl cinnamate, vinyl chloride, vinyl bromide, butadiene, vinylene carbonate, itaconic acid, itaconic acid ester, fumaric acid, fumaric acid ester, maleic acid and maleic acid ester. If the zwitterionic polymer containing the repeating unit represented by Formula (1) above is to be used as a protein stabilizer, other monomer is preferably N,N'-dimethylacrylamide, butyl (meth)acrylate or polyethylene glycol mono(meth)acrylate in view of the balance considering solubility in a solvent. Furthermore, while the amount of other monomer to be blended is arbitrary and can appropriately be selected, in order to bring out the performance of the zwitterionic polymer containing the repeating unit represented by Formula (1) above, the content of other monomer to be blended is preferably 90 mol % or less and more preferably 70 mol % or less.

The sulfide monomer represented by Formula (2) above may be used directly in the bulk state for polymerization, or may be added with a solvent to be subjected to solution polymerization, suspension polymerization or emulsion polymerization. The solvent is not particularly limited and any general solvent can be used as long as the sulfide monomer represented by Formula (2) above can be dissolved therein. For example, it can be selected from polar aprotic solvents such as acetone, dioxane, dimethylformamide (DMF), dimethyl sulfoxide (DMSO) and tetrahydrofuran (THF), and polar protic solvents such as methanol and water.

The radical polymerization of the sulfide monomer represented by Formula (2) above can be carried out by thermal polymerization or photopolymerization. The thermal polymerization can be carried out with a thermal polymerization initiator. Examples of the thermal polymerization initiator include a peroxide-based radical initiator (benzoyl peroxide, ammonium peroxide, etc.) and an azo-based radical initiator (azobisisobutyronitrile (AIBN), 2,2'-azobis-dimethylvaleronitrile (ADVN), etc.), 2,2'-azobiscyanovaleric acid (ACVA), azobis[2-(2-imidazoline-2-yl)propane]dihydrochloride (VA-044) and a water- or oil-soluble redox-based radical initiator (made from dimethylaniline and benzoyl peroxide).

In general, the amount of the radical initiator used is preferably 0.01 to 10 parts by mass and more preferably 0.01 to 5 parts by mass relative to 100 parts by mass of the sulfide monomer represented by Formula (2) above. The polymerization temperature and the polymerization time may be selected appropriately according to the type of the radical initiator and the presence of other monomer. For example, if the sulfide monomer represented by Formula (2) above solely is polymerized using AIBN as a polymerization initiator, the polymerization temperature is 40-90° C., preferably 50-80° C. and more preferably 60-70° C. The polymerization time is 1-48 hours, preferably 1-24 hours and more preferably 2-24 hours.

The photopolymerization can be carried out, for example, by irradiation with ultraviolet (UV) at a wavelength of 254 nm, an electron beam (EB) at an accelerating voltage of 150-300 kV, or the like. In this regard, while use of a photopolymerization initiator is optional, use thereof is favorable from the viewpoint of the reaction time. Examples of the photopolymerization initiator include 2-hydroxy-2-methyl-1-phenyl-1-propanone and 1-hydroxy-cyclohexyl phenyl ketone, where preferable examples specifically include 2-hydroxy-2-methyl-1-phenyl-1-propanone in view of solubility and the like.

For the radical polymerization of the sulfide monomer represented by Formula (2) above, a chain transfer agent may be used. Examples of the chain transfer agent include 2-mercaptoethanol, 1-mercapto-2-propanol, 3-mercapto-1-propanol, p-mercaptophenol, mercaptoacetic acid, 2-mercaptopropionic acid, 3-mercaptopropionic acid and 2-mercaptonicotinic acid. For example, if a sulfide monomer represented by Formula (2) above in which $R^3$ is a hydroxyl group is to be used, the chain transfer agent is preferably 2-mercaptoethanol considering solubility in the polymerization solvent, The radical polymerization of the sulfide monomer represented by Formula (2) above may also be carried out by a living radical polymerization process. Specifically, an atom transfer radical polymerization process (ATRP process), a reversible addition-fragmentation chain transfer polymerization process (RAFT polymerization process), a nitroxide-mediated polymerization process (NMP process) and the like are available. In particular, for a protein stabilizer application, the reversible addition-fragmentation chain transfer polymerization process (RAFT polymerization process) is favorable because it does not use a metal and it does not lower the enzymatic activity. Any known RAFT polymerization process can be employed. For example, processes described in WO99/31144, WO98/01478, U.S. Pat. No. 6,153,705 and H. Mori, Macromolecular Rapid Communications, 2012, 33, 1090-1107 are useful.

If the sulfide monomer represented by Formula (2) above is to be polymerized by a RAFT polymerization, a RAFT agent may be added upon a usual radical polymerization. This RAFT agent may be selected from 4-cyanopentanoic acid dithiobenzoate, 2-cyano-2-propyl benzodithioate, benzyl benzodithioate, 2-phenyl-2-propyl benzodithioate, methyl 2-phenyl-2-(phenyl-carbonothioylthio)acetate, 4-cyano-4-(phenylcarbonothioylthio)pentanoic acid N-succinimidyl ester, 4-cyano-4-(dodecylsulfanyl-thiocarbonyl) sulfanylpentanoic acid, 4-cyano-4-(dodecylsulfanyl-thiocarbonyl)sulfanyl pentanol, 2-cyano-2-propyldodecyl trithiocarbonate, 2-(dodecylthiocarbonyl thioylthio)-2-methylpropionic acid, 4-cyano-4-(dodecylsulfanyl-thiocarbonyl)sulfanylpentanoic acid polyethylene glycol methyl ether ester, 2-(dodecylthiocarbonyl thioylthio)-2-methylpropionic acid 3-azido-1-propanol ester, benzyl 1H-pyrrole-1-carbodithioate, 2-cyanopropane-2-yl-N-methyl-N-pyridine 4-yl carbodithioate and S-2-ethyl propionate-O-ethyl xanthate. For example, if a sulfide monomer represented by Formula (2) above in which $R^3$ is a hydroxyl group is used, the RAFT agent is preferably 4-cyanopentanoic acid dithiobenzoate, 4-cyano-4-(dodecylsulfanyl-thiocarbonyl)sulfanylpentanoic acid or benzyl 1H-pyrrole-1-carbodithioate in view of combination of a controllably polymerizable monomer and the RAFT agent.

In general, the amount of the RAFT agent used is preferably 0.01 to 20 parts by mass and more preferably 0.01 to 5 parts by mass relative to 100 parts by mass of the sulfide monomer represented by Formula (2) above.

The above-described living radical polymerization process, but not limited thereto, can be employed to obtain a block copolymer from the monomer represented by Formula (2) above. For example, the monomer represented by Formula (2) or the above-described other monomer can be used in a living radical polymerization process to produce Block A. Using the obtained Block A as an initiator for macromolecular polymerization, the sulfide monomer represented by Formula (2) above or the above-described other monomer can be polymerized by a living radical polymerization process to produce Block B that is coupled to Block A. If the zwitterionic polymer containing the repeating unit represented by Formula (1) above is to be used as a protein stabilizer, other monomer is preferably butyl (meth)acrylate or polyethylene glycol mono(meth)acrylate considering solubility in the solvent. Moreover, while the amount of other monomer to be blended is arbitrary and can appropriately be selected, in order to bring out the performance of the zwitterionic polymer containing the repeating unit represented by Formula (1) above, the content of other monomer to be blended is preferably 90 mol % or less and more preferably 70 mol % or less.

A sulfide polymer obtained by polymerizing the sulfide monomer represented by Formula (2) above may be used directly without purification, or preferably after isolation or purification by a treatment such as distillation of the excess solvent under reduced pressure, reprecipitation, gel filtration chromatography or dialysis.

[Step B]

[Step B] is a step of allowing the sulfide polymer obtained in [Step A] above to react with a sulfide-reactive compound represented by Formula (3).

[Chemical formula 10]

$$X—CH_2—R^2 \qquad (3)$$

In Formula (3) above, X is not particularly limited as long as it can react with the sulfide polymer, where it is selected from a chlorine atom, a bromine atom, an iodine atom, a mesyl group (a methanesulfonyl group), a tosyl group (p-toluenesulfonyl group) and a trifluoromethanesulfonyl group. It is preferably a bromine atom or an iodine atom and more preferably an iodine atom.

In Formula (3) above, $R^2$ is not particularly limited and can likely be defined as $R^1$ in Formula (1). In Formula (3), $R^2$ is selected from a hydrogen atom, a linear, branched or cyclic C1-C6 alkyl group or a C6-C20 aromatic group.

Examples of the linear alkyl group include a methyl group, an ethyl group, a propyl group, a n-butyl group, a pentyl group and a hexyl group; examples of the branched alkyl group include an isopropyl group and a 2-butyl group; and examples of the cyclic alkyl group include a cyclopentyl group and a cyclohexyl group. The carbon number of the alkyl group is preferably 1-4 and more preferably 1-3.

Moreover, examples of an aromatic substituent include a phenyl group, a p-nitrophenyl group, a bromophenyl group, phenylboronic acid, a hydroxyphenyl group, a dihydroxyphenyl group and a trihydroxyphenyl group. The carbon number of the aromatic group is preferably 6-12 and more preferably 6-10.

For a protein stabilizer application, $R^2$ is preferably a hydrogen atom, a methyl group, an ethyl group or a propyl group from the viewpoint of enhancing affinity of the polymer for water.

For example, the sulfide-reactive compound represented by Formula (3) above is preferably iodomethane, iodoethane, iodopropane or iodobutane from the viewpoint of maintaining affinity of a zwitterionic polymer for water.

The solvent used for reacting the sulfide polymer and the sulfide-reactive compound represented by Formula (3) above is not particularly limited and any general solvent can be used as long as the sulfide polymer and the sulfide-reactive compound can be dissolved therein. For example, it can be selected from polar aprotic solvents such as acetone, dioxane, dimethylformamide (DMF), dimethyl sulfoxide (DMSO) and tetrahydrofuran (THF), and polar protic solvents such as methanol. The amount of the solvent used is 1-100 times, preferably 1-50 times and most preferably 1-30 times the amount of the sulfide polymer in mass ratio.

The amount of the sulfide-reactive compound represented by Formula (3) above used is 0.1-100 times, preferably 0.1-50 times and most preferably 0.1-30 the amount of the sulfide polymer in mass ratio.

While the temperature of the reaction between the sulfide polymer and the sulfide-reactive compound represented by Formula (3) above depends on the solvent used, it is usually in a range of −20-100° C., preferably 0-70° C. and most preferably 20-50° C. While the reaction time depends on the reaction temperature, the molecular weight of the sulfide polymer used and the type of the sulfide-reactive compound, it is usually about 1-72 hours and more preferably 1-24 hours.

Accordingly, the sulfide polymer is allowed to react with the sulfide-reactive compound represented by Formula (3) above to obtain a zwitterionic polymer containing the repeating unit represented by Formula (1). The obtained zwitterionic polymer can be used directly without purification, or preferably after isolation or purification by a treatment such as distillation of the excess sulfide-reactive compound under reduced pressure, reprecipitation, gel filtration chromatography or dialysis.

<Polymerization of Zwitterionic Monomer>

A zwitterionic polymer of the present invention can also be obtained by radically polymerizing the zwitterionic monomer represented by Formula (4) below.

[Chemical formula 11]

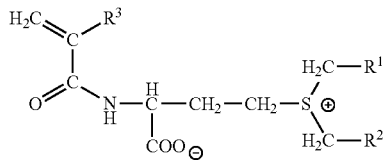

(4)

In Formula (4), $R^1$ and $R^2$ each independently represent a substituent which is selected from, but not particularly limited to, a hydrogen atom, a linear, branched or cyclic C1-C6 alkyl group, a C6-C20 aromatic group or a C1-C6 alkylene group in which $R^1$ and $R^2$ are linked to each other.

Examples of the linear alkyl group include a methyl group, an ethyl group, a propyl group, a n-butyl group, a pentyl group and a hexyl group; examples of the branched alkyl group include an isopropyl group and a 2-butyl group; and examples of the cyclic alkyl group include a cyclopentyl group and a cyclohexyl group. The carbon number of the alkyl group is preferably 1-4 and more preferably 1-3.

Moreover, the aromatic group is, for example, a phenyl group, a p-nitrophenyl group, a bromophenyl group, phenylboronic acid, a hydroxyphenyl group, a dihydroxyphenyl group or a trihydroxyphenyl group. The carbon number of the aromatic group is preferably 6-12 and more preferably 6-10.

A C1-C6 alkylene group in which $R^1$ and $R^2$ are linked to each other is, for example; a substituent represented by Formula (7) below.

For a protein stabilizer application, $R^1$ and $R^2$ are preferably any of a hydrogen atom, a methyl group, an ethyl group or a propyl group from the viewpoint of enhancing affinity of the polymer for water.

[Chemical formula 12]

(7)

(In Formula (7), in represents an integer from 1 to 6, preferably 2-6 and more preferably an integer of 2-4).

In Formula (4) above, $R^3$ represents a hydrogen atom or a methyl group.

Examples of the zwitterionic monomer represented by Formula (4) above include a zwitterionic polymer in which $R^1$ and $R^2$ are both hydrogen atoms and $R^3$ is a hydrogen atom, a zwitterionic polymer in which $R^1$ is a propyl group, $R^2$ is a hydrogen atom and $R^3$ is a hydrogen atom, and a zwitterionic polymer in which $R^1$ is a benzyl group, $R^2$ is a hydrogen atom and $R^3$ is a hydrogen atom. For the sake of facilitating the synthesis, it is preferably a zwitterionic polymer in which $R^1$ and $R^2$ are both hydrogen atoms and $R^3$ is a hydrogen atom.

The zwitterionic monomer represented by Formula (4) above can be produced by allowing the sulfide monomer represented by Formula (2) above to react with the sulfide-reactive compound represented by Formula (3) above.

The solvent used for reacting the sulfide monomer represented by Formula (2) above and the sulfide-reactive compound represented by Formula (3) above is not particularly limited and any general solvent can be used as long as the sulfide polymer and the sulfide-reactive compound can be dissolved therein. For example, it can be selected from polar aprotic solvents such as acetone, dioxane, dimethylformamide (DMF), dimethyl sulfoxide (DMSO) and tetrahydrofuran (THF), and polar protic solvents such as methanol. The amount of the solvent used is 1-100 times, preferably 1-50 times and most preferably 1-30 times the amount of the sulfide polymer in mass ratio.

The amount of the sulfide-reactive compound represented by Formula (3) above used is 0.1-100 times, preferably 0.1-50 times and most preferably 0.1-30 times the amount of the sulfide monomer represented by Formula (2) above in mass ratio.

While the temperature of the reaction between the sulfide monomer represented by Formula (2) above and the sulfide-reactive compound represented by Formula (3) above depends on the solvent used, it is usually in a range of −20-100° C., preferably 0-70° C. and most preferably 20-50° C. While the reaction time depends on the reaction temperature, the molecular weight of the sulfide polymer used and the type of the sulfide-reactive compound, it is usually about 1-72 hours and more preferably 1-24 hours.

Accordingly, the sulfide monomer represented by Formula (2) above is allowed to react with the sulfide-reactive compound represented by Formula (3) above to obtain a zwitterionic monomer represented by Formula (4) above. The obtained zwitterionic polymer can be used directly without purification, or preferably after isolation or purification by a treatment such as distillation of the excess sulfide-reactive compound under reduced pressure, reprecipitation or column chromatography.

Similar to the monomer represented by Formula (2) above, the zwitterionic monomer represented by Formula (4) above may be obtained via polymerization solely, i.e., only one or two or more types, of monomers of Formula (4), or via polymerization of a mixture with other monomer that is copolymerizable with the zwitterionic monomer represented by Formula (4) above.

Other monomer can appropriately be selected in accordance with the application, where examples thereof include: various (meth)acrylate esters such as diethylaminoethyl (meth)acrylate, polyethylene glycol mono(meth)acrylate, glycerol (meth)acrylate, (meth)acryloyloxy ethyl phosphate, (meth)acryloyloxy ethyl phosphorylcholine, N-methyl carboxybetaine (meth)acrylate, N-methyl sulfobetaine (meth)acrylate, ethyl (meth)acrylate, propyl (meth)acrylate, butyl (meth)acrylate, pentyl (meth)acrylate, hexyl (meth)acrylate, stearyl (meth)acrylate, glycidyl (meth)acrylate, dimethylamino ethyl (meth)acrylate, 2-methacrylate and 2-methoxyethyl (meth)acrylate; various vinyl ethers such as methyl vinyl ether; as well as various radically-polymerizable monomers such as acrylamide, N,N'-dimethylacrylamide, N-isopropyl (meth)acrylamide, (meth)acrylic acid, allyl alcohol, acrylonitrile, acrolein, vinyl acetate, sodium vinylsulfonate, styrene, chlorostyrene, vinylphenol, vinyl cinnamate, vinyl chloride, vinyl bromide, itaconic acid, itaconic acid ester, fumaric acid and maleic acid. If the zwitterionic polymer containing the repeating unit represented by Formula (1) above is to be used as a protein stabilizer, other monomer is preferably N,N'-dimethylacrylamide or polyethylene glycol mono(meth)acrylate in view of the balance considering solubility in a solvent. Furthermore, while the amount of other monomer to be blended is arbitrary and can appropriately be selected, in order to bring out the performance of the zwitterionic polymer containing the repeating unit represented by Formula (1) above, the content of other monomer to be blended is preferably 90 mol % or less and more preferably 70 mol % or less.

Alternatively, the zwitterionic monomer represented by Formula (4) above may be added with a solvent to be subjected to solution polymerization, suspension polymerization or emulsion polymerization. The solvent is not particularly limited as long as the zwitterionic monomer represented by Formula (4) above can be dissolved therein and polymerization proceeds. For example, a mixed solvent of an alcohol-based solvent such as methanol and water may be used. The ratio of alcohol and water in the mixed solvent is such that the volume percent of the alcohol-based solvent is preferably 50% or less and more preferably 10% or less.

The polymerization of the zwitterionic monomer represented by Formula (4) above can be carried out by thermal polymerization or photopolymerization. The thermal polymerization can be carried out with a thermal polymerization initiator. While the thermal polymerization initiator may be selected, for example, from a peroxide-based radical initiator (benzoyl peroxide, ammonium peroxide, etc.), an azo-based radical initiator (azobisisobutyronitrile (AIBN), 2,2'-azobis-dimethylvaleronitrile (ADVN), etc.), 2,2'-azobiscyanovaleric acid (ACVA) or azobis[2-(2-imidazoline-2-yl)propane]dihydrochloride (VA-044), it is preferably ACVA or VA-044 and more preferably VA-044 considering solubility in an aqueous solvent. In general, the amount of the radical initiator used is preferably 0.01 to 10 parts by mass and more preferably 0.01 to 5 parts by mass relative to 100 parts by mass of the zwitterionic monomer represented by Formula (4) above. The polymerization temperature and the polymerization time may be appropriately selected according to the type of the radical initiator and the presence of other monomer. For example, if the zwitterionic monomer represented by Formula (4) above is solely polymerized using VA-044, the polymerization temperature is 30-70° C., preferably 35-65° C. and more preferably 35-50° C. The polymerization time is 1-48 hours, preferably 1-24 hours and more preferably 2-24 hours.

The photopolymerization can be carried out, for example, by irradiation with ultraviolet (UV) at a wavelength of 254 nm, an electron beam (EB) at an accelerating voltage of 150-300 kV, or the like. In this regard, while use of a photopolymerization initiator is optional, use thereof is favorable from the viewpoint of the reaction time. Examples of the photopolymerization initiator include 2-hydroxy-2-methyl-1-phenyl-1-propanone, 1-hydroxy-cyclohexyl phenyl ketone and lithium phenyl(2,4,6-trimethylbenzoyl)phosphinate, where preferable examples specifically include lithium phenyl(2,4,6-trimethylbenzoyl)phosphinate in view of solubility in an aqueous solvent and the like.

For the radical polymerization of the zwitterionic monomer represented by Formula (4) above, a chain transfer agent may be used. Examples of the chain transfer agent include 2-mercaptoethanol, 1-mercapto-2-propanol, 3-mercapto-1-propanol, p-mercaptophenol, mercaptoacetic acid, 2-mercaptopropionic acid, 3-mercaptopropionic acid and 2-mercaptonicotinic acid. For example, if a zwitterionic monomer represented by Formula (4) above in which $R^3$ is a hydroxyl group is to be used, the chain transfer agent is preferably mercaptoacetic acid or 2-mercaptopropionic acid considering solubility in the polymerization solvent.

The radical polymerization of the zwitterionic monomer represented by Formula (4) above may also be carried out by a living radical polymerization process. Specifically, an atom transfer radical polymerization process (ATRP process), a reversible addition-fragmentation chain transfer polymerization process (RAFT polymerization process), a nitroxide-mediated polymerization process (NMP process) and the like are available. In particular, for a protein stabilizer application, the reversible addition-fragmentation chain transfer polymerization process (RAFT polymerization process) is favorable because it does not use a metal and it does not lower the enzymatic activity. Any known RAFT polymerization process can be employed. For example, processes described in WO99/31144, WO98/01478 and U.S. Pat. No. 6,153,705 are useful.

If the zwitterionic monomer represented by Formula (4) above is to be polymerized by a RAFT polymerization, a RAFT agent may be added upon a usual radical polymerization. This RAFT agent may be selected from 4-cyanopentanoic acid dithiobenzoate, 2-cyano-2-propyl benzodithioate, benzyl benzodithioate, 2-phenyl-2-propyl benzodithioate, methyl 2-phenyl-2-(phenyl-carbonothioylthio)acetate, 4-cyano-4-(phenylcarbonothioylthio)pentanoic acid N-succinimidyl ester, 4-cyano-4-(dodecylsulfanyl-thiocarbonyl)sulfanylpentanoic acid, 4-cyano-4-(dodecylsulfanyl-thiocarbonyl)sulfanyl pentanol, 2-cyano-2-propyldodecyl trithiocarbonate, 2-(dodecylthiocarbonyl thioylthio)-2-methylpropionic acid, 4-cyano-4-(dodecylsulfanyl-thiocarbonyl)sulfanylpentanoic acid polyethylene glycol methyl ether ester, 2-(dodecylthiocarbonyl thioylthio)-2-methylpropionic acid 3-azido-1-propanol ester, benzyl 1H-pyrrole-1-carbodithioate, 2-cyanopropane-2-yl-N-methyl-N-pyridine 4-yl carbodithioate and S-2-ethyl propionate-O-ethyl xanthate. For example, if a zwitterionic monomer represented by Formula (4) above in which $R^3$ is a hydroxyl group is used, the RAFT agent is preferably 4-cyanopentanoic acid dithiobenzoate, 4-cyano-4-(dodecylsulfanyl-thiocarbonyl)sulfanylpentanoic acid or 4-cyano-4-(dodecylsulfanyl-thiocarbonyl)sulfanylpentanoic acid polyethylene glycol methyl ether ester considering solubility of the RAFT agent.

In general, the amount of the RAFT agent used is preferably 0.01 to 20 parts by mass and more preferably 0.01 to 10 parts by mass relative to 100 parts by mass of the zwitterionic monomer represented by Formula (4) above.

The above-described living radical polymerization process, but not limited thereto, can be employed to obtain a block copolymer from the zwitterionic monomer represented by Formula (4) above. For example, the zwitterionic monomer represented by Formula (4) above or the above-described other monomer can be used in a living radical polymerization process to produce Block A. Using the Obtained Block A as an initiator for macromolecular polymerization, the zwitterionic monomer represented by Formula (4) above or the above-described other monomer can be polymerized by a living radical polymerization process to produce Block B that is coupled to Block A. If the zwitterionic polymer containing the repeating unit represented by Formula (1) above is to be used as a protein stabilizer, other monomer is preferably N, N'-dimethylacrylamide, butyl (meth)acrylate or polyethylene glycol mono(meth)acrylate considering solubility in the solvent. Moreover, while the amount of other monomer to be blended is arbitrary and can appropriately be selected, in order to bring out the performance of the zwitterionic polymer containing the repeating unit represented by Formula (1) above, the content of other monomer to be blended is preferably 90 mol % or less and more preferably 70 mol % or less.

A zwitterionic polymer containing the repeating unit represented by Formula (1) above obtained by polymerizing the zwitterionic monomer represented by Formula (4) above may be used directly without purification, or preferably after isolation or purification by a treatment such as distillation of the excess solvent under reduced pressure, reprecipitation, gel filtration chromatography or dialysis.

<Protein Stabilizer>

A protein stabilizer of the present invention contains a zwitterionic polymer having the repeating unit represented by Formula (1) above. The protein stabilizer is preferably an aqueous solution of the zwitterionic polymer where water is preferably purified water, pure water, ion exchange water or the like, and more preferably a buffer containing water. Any buffer commonly used in this field can be used as long as it does not inhibit physiological activities such as enzymatic activity and antigenicity of the protein. Examples of the buffer include a phosphate buffer, a Tris buffer, Good's buffer, a glycine buffer, a borate buffer and an acetate buffer, where a phosphate buffer or an acetate buffer is particularly preferable.

The content of the zwitterionic polymer containing the repeating unit represented by Formula (1) above in a protein stabilizer solution is preferably 0.01 mass % or more and more preferably 0.1 mass % or more. While the upper limit value of the content is not particularly limited as long as the polymer is soluble in water, i.e., the main solvent, it is, for example, 20 mass % or less and preferably 10 mass % or less. Within this range, the protein stabilizer solution will exhibit a significant protein-stabilizing effect and will facilitate protein dissolution or mixing with a protein solution.

A protein to be stabilized with the protein stabilizer of the present invention is not particularly limited. Examples of such protein include acetylcholinesterase, alkaline phosphatase, β-D-galactosidase, glucoamylase, glucose oxidase, glucose-6-phosphate dehydrogenase, hexokinase, penicillinase, peroxidase and lysozyme, preferably peroxidase and alkaline phosphatase that are generally used in an enzyme immunoassay.

The protein stabilizer of the present invention may be used by adding it to a protein solution. Alternatively, the protein stabilizer of the present invention may be used as a protein stabilizer solution in which a protein of interest can be dissolved. Furthermore, a protein solution and a protein stabilizer solution may be prepared and then mixed together.

In order to stabilize a protein with the protein stabilizer of the present invention, the temperature for keeping the protein-stabilizing solution is preferably 2-40° C. This is because the protein-stabilizing solution may freeze if the temperature is 2° C. or lower while the duration of protein stabilization may be shortened if the temperature is 40° C. or higher.

EXAMPLES

Hereinafter, the present invention will be described more specifically by means of examples, although the present invention is not limited to the following examples. In each synthesis example, JMTC-400 manufactured by JEOL Ltd. was used for nuclear magnetic resonance ($^1$H-NMR).

Example 1: Synthesis of Polymer A

Synthesis Example 1-1: Synthesis of Monomer 2

[Chemical formula 13]

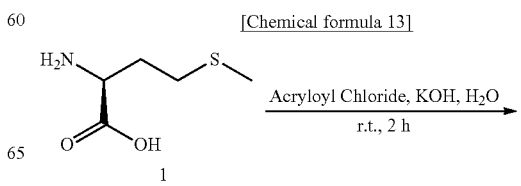

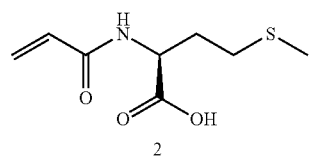

L-methionine (1) (15.0 g, 74.0 mmol) was placed into a four-neck flask to be dissolved in 200 ml of a 5 mass % aqueous potassium hydroxide solution. The reaction solution was cooled to 0° C., into which acryloyl chloride (15.0 ml, 141 mmol) was dropped by spending 15 minutes. Subsequently, the temperature of the reaction system was raised to room temperature and the reaction system was agitated for 2 hours. 50 ml of 4N hydrochloric acid was added to the reaction solution to adjust pH to 2.0, and the organic phase was extracted with 100 ml of ethyl acetate for three times. The organic phase was washed twice with 100 ml of saturated saline solution and then dried with magnesium sulfate. The solvent was distilled away under reduced pressure. The resulting mixture was purified by silica gel chromatography (ethyl acetate/methanol=1/1 v/v) to give Monomer 2.

Yield 9.9 g $^1$H-NMR (CD$_3$OD, 400 MHz)

6.2-6.4 ppm (C$\underline{H}_2$=CH, m, 2H), 5.65 ppm (CH$_2$=C$\underline{H}$, t, 1H), 4.63 ppm (NH—C$\underline{H}$—COOH, t, 1H), 2.4-2.6 ppm (CH$_2$—C$\underline{H}_2$—S, m, 2H), 2.0-2.2 ppm (C$\underline{H}_2$—CH$_2$—S, m, 2H), 1.92 ppm (S—C$\underline{H}_3$, s, 3H)

Synthesis Example 1-2: Synthesis of Polymer 3

[Chemical formula 14]

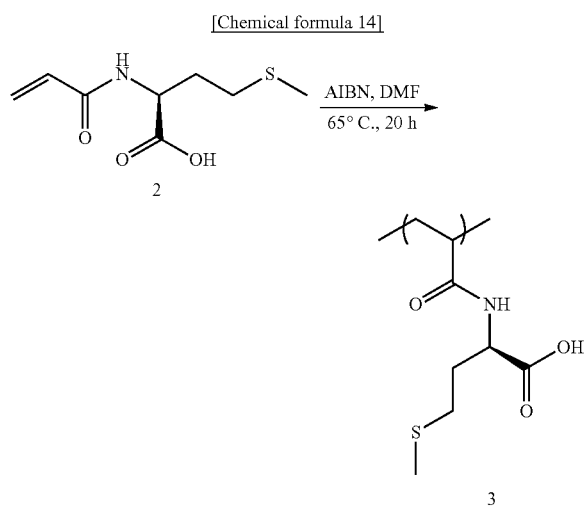

Monomer 2 (1.50 g, 7.50 mmol) and azobisisobutyronitrile (12 mg, 0.08 mmol) were placed into a two-neck flask to be dissolved in DMF (4 ml). Following 15 minutes of nitrogen bubbling, the temperature of the reaction system was raised to 65° C. to initiate polymerization. After 20 hours, the reaction solution was reprecipitated with 200 ml of MTBE to give Polymer 3.

Yield 1.4 g $^1$H-NMR (CD$_3$OD, 400 MHz)

4.3-4.6 ppm (NH—C$\underline{H}$—COOH), 2.6-2.8 ppm (CH$_2$—C$\underline{H}_2$—S), 2.0-2.6 ppm (C$\underline{H}_2$—CH$_2$—S, S—C$\underline{H}_3$), 1.6-2.6 ppm (main chain of the polymer)

Synthesis Example 1-3: Synthesis of Polymer A

[Chemical formula 15]

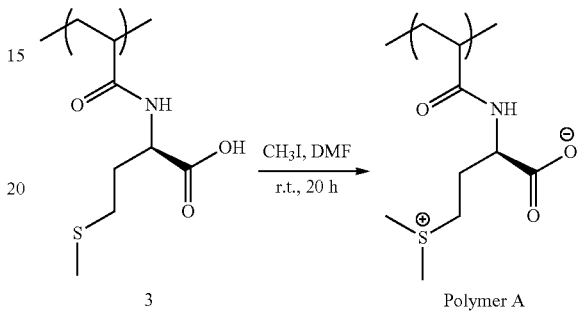

Polymer 3 (1.0 g) was placed into an eggplant-shaped flask to be dissolved in 3 ml of DMF. 1 ml of iodomethane was added to the reaction solution and the resultant was agitated at room temperature for 20 hours. The reaction solution was reprecipitated with 50 ml of acetone to give Polymer A.

Yield 1.1 g $^1$H-NMR (D$_2$O, 400 MHz)

4.3-4.6 ppm (NH—C$\underline{H}$—COOH), 3.2-3.4 ppm (CH$_2$—C$\underline{H}_2$—S(CH$_3$)$_2$), 2.8-3.0 ppm (CH$_2$—S(C$\underline{H}_3$)$_2$), 1.4-2.4 ppm (C$\underline{H}_2$—CH$_2$—S, main chain of the polymer)

The number-average molecular weight and molecular weight distribution (weight-average molecular weight/number-average molecular weight) of Polymer A obtained were determined by gel permeation chromatography measurement using a differential refractometer as a detector. LC-720AD manufactured by Shimadzu Corporation was used as a pump, RID10A manufactured by Shimadzu Corporation was used as a detector (differential refractometer), and SPD-20A was used as a detector (UV). Two connected columns, namely, TSKGel G3000P$_{WXL}$ and TSKGel G5000P$_{WXL}$ manufactured by Tosoh Corporation (column size 4.6 mm×25 cm), were used. 50 mM phosphate buffer/acetonitrile (9/1 v/v) that was adjusted to pH 9.0 was used as the developing solvent. The measurement conditions were a flow rate of 0.6 ml/min, a column temperature of 40° C., a sample concentration of 0.2 mg/ml and a feeding amount of 70 μL. Polyethylene glycol was used as a standard. As a result of the gel permeation chromatography measurement, the number-average molecular weight and the molecular weight distribution of Polymer A were 19,000 and 1.95, respectively.

Example 2: Synthesis of Polymer B

Synthesis Example 2-1: Synthesis of Polymer 4

[Chemical formula 16]

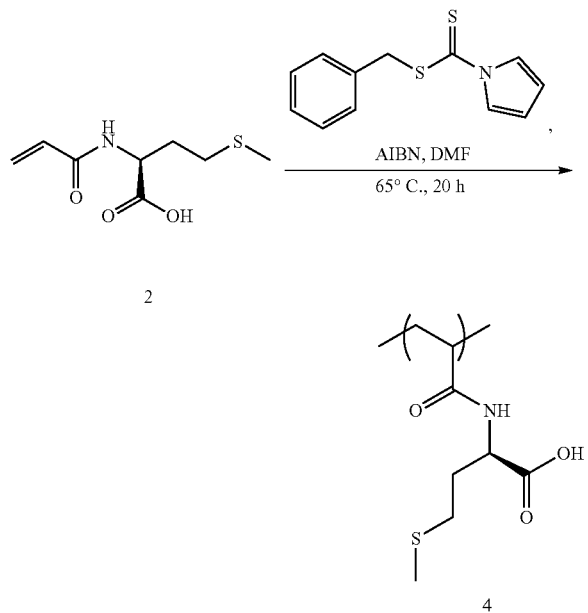

Monomer 2 (1.50 g, 7.50 mmol), benzyl 1H-pyrrole-1-carbodithioate (34.5 mg, 0.15 mmol) and azobisisobutyronitrile (12 mg, 0.08 mmol) were placed into a two-neck flask to be dissolved in DMF (4 ml). Following 15 minutes of nitrogen bubbling, the temperature of the reaction system was raised to 65° C. to initiate polymerization. After 20 hours, the reaction solution was reprecipitated with 200 ml of MTBE to give Polymer 4

Yield 1.4 g $^1$H-NMR (CD$_3$OD, 400 MHz)

4.3-4.6 ppm (NH—C$\underline{H}$—COOH), 2.6-2.8 ppm (CH$_2$—C$\underline{H_2}$—S), 2.0-2.6 ppm (C$\underline{H_2}$—CH$_2$—S, S—C$\underline{H_3}$), 1.6-2.6 ppm (main chain of the polymer)

Synthesis Example 2-2: Synthesis of Polymer B

[Chemical formula 17]

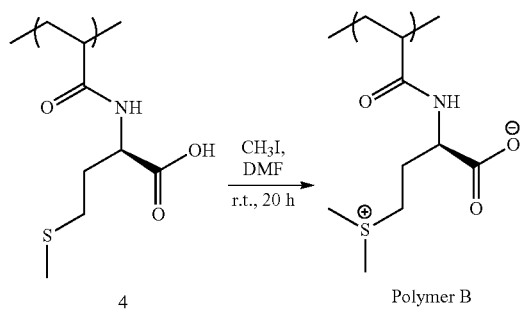

Polymer 4 (1.0 g) was placed into an eggplant-shaped flask to be dissolved in 3 ml of DMF. 1 ml of iodomethane was added to the reaction solution and the resultant was agitated at room temperature for 20 hours. The reaction solution was reprecipitated with 50 ml of acetone to give Polymer B.

Yield 1.1 g $^1$H-NMR (D$_2$O, 400 MHz)

4.3-4.6 ppm (NH—C$\underline{H}$—COOH), 3.2-3.4 ppm (CH$_2$—C$\underline{H_2}$—S(CH$_3$)$_2$), 2.8-3.0 ppm (CH$_2$—S(C$\underline{H_3}$)$_2$), 1.4-2.4 ppm (C$\underline{H_2}$—CH$_2$—S, main chain of the polymer)

The number-average molecular weight and the molecular weight distribution (weight-average molecular weight/number-average molecular weight) of Polymer B obtained were determined in the same manner as Synthesis example 3. As a result of the gel permeation chromatography measurement, the number-average molecular weight and the molecular weight distribution of Polymer A were 7,900 and 1.25, respectively.

Example 3: Synthesis of Polymer C

[Chemical formula 18]

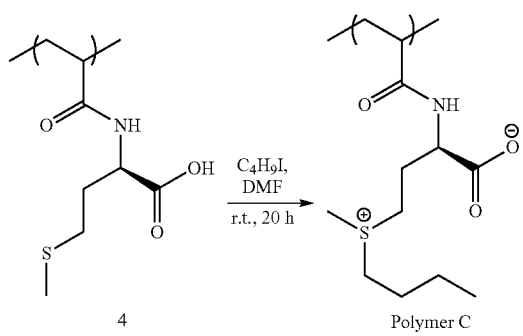

Polymer 4 (1.0 g) was placed into an eggplant-shaped flask to be dissolved in 3 ml of DMF. 1 ml of iodobutane was added to the reaction solution and the resultant was agitated at room temperature for 20 hours. The reaction solution was reprecipitated with 50 ml of acetone to give Polymer C.

Yield 1.1 g $^1$H-NMR (D$_2$O, 400 MHz)

4.3-4.6 ppm (NH—C$\underline{H}$—COOH), 3.2-3.4 ppm (CH$_2$—C$\underline{H_2}$—S(CH$_3$)$_2$), 2.8-3.0 ppm (CH$_2$—S(C$\underline{H_3}$)$_2$), 0.8-2.4 ppm (butyl group, C$\underline{H_2}$—CH$_2$—S, main chain of the polymer)

The number-average molecular weight and the molecular weight distribution of Polymer C obtained were determined in the same manner as Example 1 above. The number-average molecular weight and the molecular weight distribution of Polymer C were 8,100 and 1.23, respectively.

Example 4: Synthesis of Polymer D

Synthesis Example 4-1: Synthesis of 5

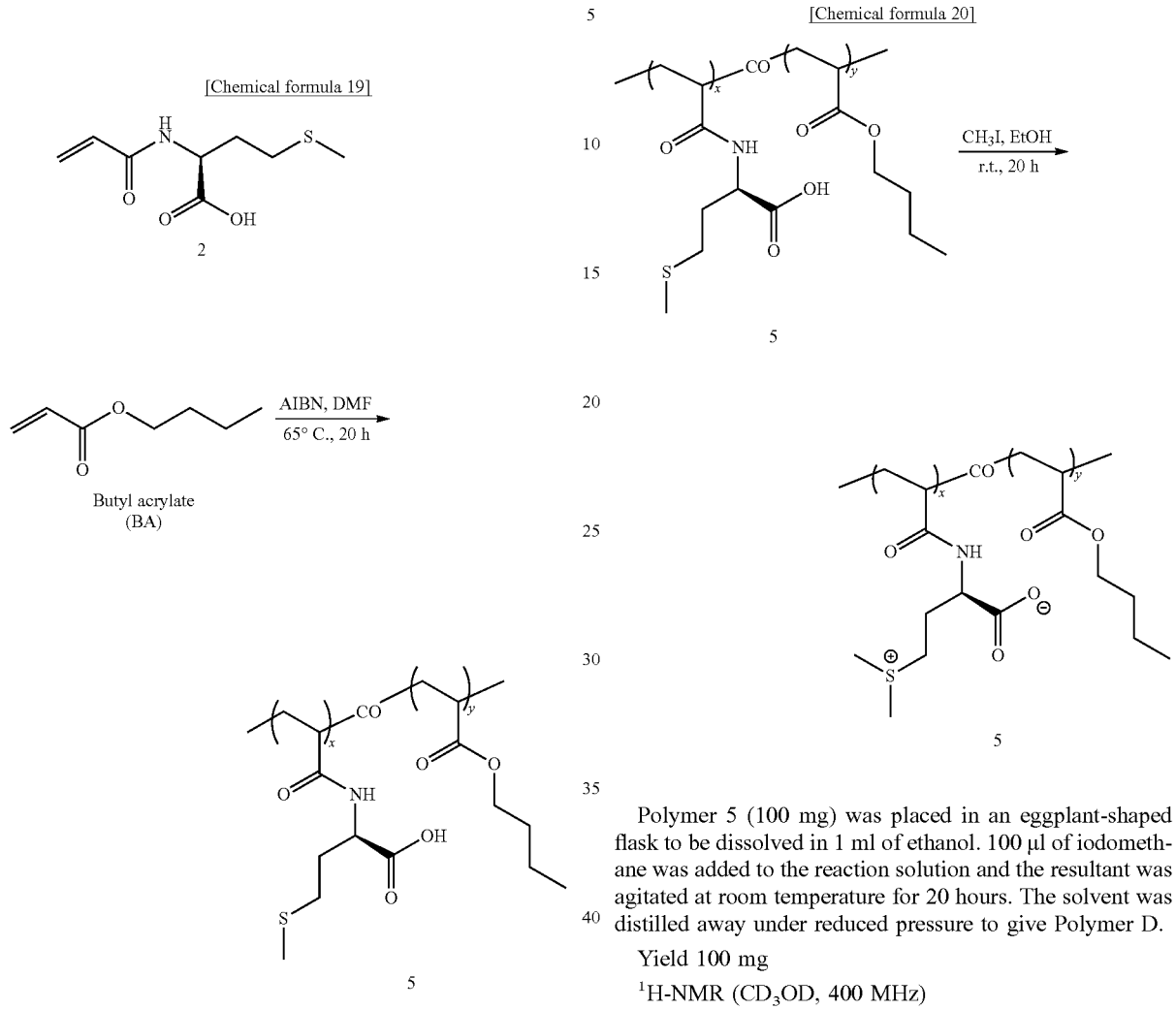

Monomer 2 (60 mg, 0.30 mmol), butyl acrylate (90 mg, 0.70 mmol) and azobisisobutyronitrile (0.1 mg, 0.01 mmol) were placed into a two-neck flask to be dissolved in ethanol (1 ml), Following 15 minutes of nitrogen bubbling, the temperature of the reaction system was raised to 65° C. to initiate polymerization. After 20 hours, the reaction solution was reprecipitated with 20 ml of MTBE to give Polymer 5.

Composition ratio (mole ratio) x:y=32:68

Yield 140 mg $^1$H-NMR, (CDCl$_3$, 400 MHz)

4.1-4.6 ppm (NH—C$\underline{H}$—COOH), 3.9-4.1 (COO—C$\underline{H}_2$—CH$_2$ (BA)), 2.6-2.8 ppm (CH$_2$—C$\underline{H}_2$—S), 2.0-2.6 ppm (C$\underline{H}_2$—CH$_2$—S, S—C$\underline{H}_3$), 1.6-2.6 ppm (C$\underline{H}_2$—C$\underline{H}_2$—CH$_3$ (BA), main chain of the polymer), 0.8-1.0 ppm (CH$_2$—C$\underline{H}_3$ (BA))

Synthesis Example 4-2: Synthesis of Polymer D

Polymer 5 (100 mg) was placed in an eggplant-shaped flask to be dissolved in 1 ml of ethanol. 100 μl of iodomethane was added to the reaction solution and the resultant was agitated at room temperature for 20 hours. The solvent was distilled away under reduced pressure to give Polymer D.

Yield 100 mg $^1$H-NMR (CD$_3$OD, 400 MHz)

4.1-4.6 ppm (NH—C$\underline{H}$—COOH, COO—C$\underline{H}_2$—CH$_2$ (BA)), 3.2-3.4 ppm (CH$_2$—C$\underline{H}_2$—S(CH$_3$)$_2$), 2.8-3.0 ppm (CH$_2$—S(C$\underline{H}_3$)$_2$), 1.0-2.4 ppm (C$\underline{H}_2$—C$\underline{H}_2$—CH$_3$ (BA), C$\underline{H}_2$—CH$_2$—S, main chain of the polymer), 0.8-1.0 ppm (CH$_2$—C$\underline{H}_3$ (BA))

The number-average molecular weight and the molecular weight distribution (weight-average molecular weight/number-average molecular weight) of Polymer D obtained were determined by gel permeation chromatography measurement using a differential refractometer as a detector.

Instruments used were the same as Example 1 above. Two connected columns, namely, Mixed-D manufactured by Agilent (particle size 5 μm, column size 4.6 mm×25 cm) were used. 0.5 mass % lithium bromide-containing chloroform/methanol=6/4 (v/v) was used as the developing solvent. The measurement conditions were a flow rate of 0.6 ml/min, a column temperature of 40° C., a sample concentration of 0.2 mg/ml and a feeding amount of 70 μl. Polyethylene glycol was used as a standard. As a result of the gel permeation chromatography measurement, the number-average molecular weight and the molecular weight distribution of Polymer D were 21,000 and 2.06, respectively.

Example 5: Synthesis of Polymer E

Synthesis Example 5-1: Synthesis of Polymer 6

[Chemical formula 21]

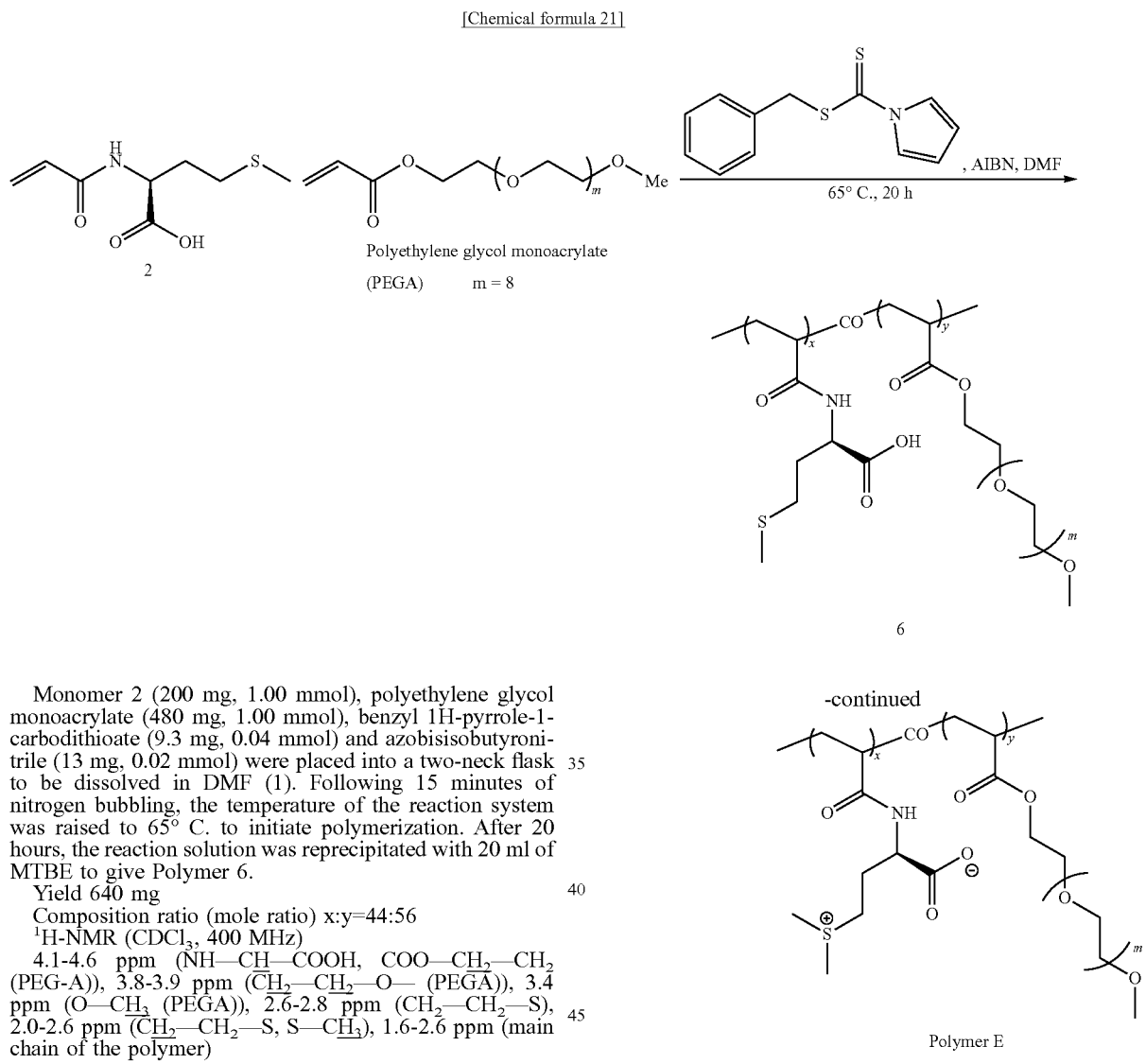

Monomer 2 (200 mg, 1.00 mmol), polyethylene glycol monoacrylate (480 mg, 1.00 mmol), benzyl 1H-pyrrole-1-carbodithioate (9.3 mg, 0.04 mmol) and azobisisobutyronitrile (13 mg, 0.02 mmol) were placed into a two-neck flask to be dissolved in DMF (1). Following 15 minutes of nitrogen bubbling, the temperature of the reaction system was raised to 65° C. to initiate polymerization. After 20 hours, the reaction solution was reprecipitated with 20 ml of MTBE to give Polymer 6.

Yield 640 mg

Composition ratio (mole ratio) x:y=44:56

$^1$H-NMR (CDCl$_3$, 400 MHz)

4.1-4.6 ppm (NH—C$\underline{H}$—COOH, COO—C$\underline{H_2}$—CH$_2$ (PEG-A)), 3.8-3.9 ppm (C$\underline{H_2}$—CH$_2$—O— (PEGA)), 3.4 ppm (O—C$\underline{H_3}$ (PEGA)), 2.6-2.8 ppm (CH$_2$—C$\underline{H_2}$—S)), 2.0-2.6 ppm (C$\underline{H_2}$—CH$_2$—S, S—C$\underline{H_3}$), 1.6-2.6 ppm (main chain of the polymer)

Synthesis Example 5-2: Synthesis of Polymer E

[Chemical formula 22]

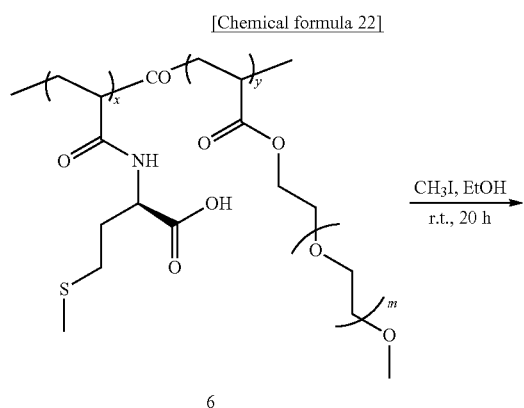

Polymer 6 (100 mg) was placed into an eggplant-shaped flask to be dissolved in 1 ml of ethanol. 100 µl of iodomethane was added to the reaction solution and the resultant was agitated at room temperature for 20 hours. The solvent was distilled away under reduced pressure to give Polymer E.

Yield 100 mg $^1$H-NMR (D$_2$O, 400 MHz)

4.1-4.6 ppm (NH—C$\underline{H}$—COOH, COO—C$\underline{H_2}$—CH$_2$ (PEGA)), 3.8-3.9 ppm (C$\underline{H_2}$—CH$_2$—O— (PEGA)), 3.2-3.4 ppm (O—C$\underline{H_3}$ (PEGA), CH$_2$—C$\underline{H_2}$—S(CH$_3$)$_2$), 2.8-3.0 ppm (CH$_2$—S(C$\underline{H_3}$)$_2$), 1.6-2.4 ppm (main chain of the polymer)

The number-average molecular weight and the molecular weight distribution (weight-average molecular weight/number-average molecular weight) of Polymer E obtained were determined by gel permeation chromatography measurement using a differential refractometer as a detector.

Instruments used were the same as Example 1 above. Two connected columns, namely, Mixed-D manufactured by Agilent (particle size 5 μm, column size 4.6 mm×25 cm) were used. 11.5 mM lithium bromide-containing dimethylformamide was used as the developing solvent. The measurement conditions were a flow rate of 0.6 ml/min, a column temperature of 40° C., a sample concentration of 0.2 mg/ml and a feeding amount of 70 Polyethylene glycol was used as a standard. As a result of the gel permeation chromatography measurement, the number-average molecular weight and the molecular weight distribution of Polymer E were 15,000 and 1.30, respectively.

Example 6: Synthesis of Polymer F

Synthesis Example 6-1: Synthesis of Monomer 7

[Chemical formula 23]

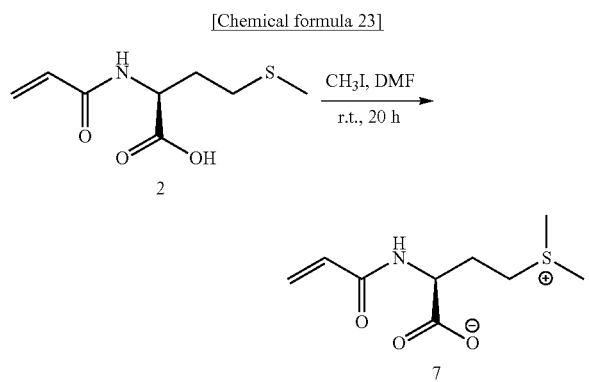

Monomer 2 (609 mg, 3.00 mmol) was placed into an eggplant-shaped flask to be dissolved in 6 ml of DMF. Iodomethane (210 μl, 3.30 mmol) was added to the reaction solution and the resultant was agitated at room temperature for 20 hours. The reaction solution was added to 100 ml of MTBE for crystallization. The resulting compound was dissolved in 4 ml of methanol and crystallized again with 100 ml of MTBE to give Monomer 7.

Yield 600 mg $^1$H-NMR (D$_2$O, 400 MHz)

6.2-6.4 ppm (C$\underline{H}_2$=CH, m, 2H), 5.65 ppm (CH$_2$=C$\underline{H}$, t, 1H), 4.63 ppm (NH—C$\underline{H}$—COOH, t, 1H), 3.48 ppm (CH$_2$—C$\underline{H}_2$—S, t, 2H), 3.05 ppm (CH$_2$—S(C$\underline{H}_3$)$_2$, s, 6H), 2.2-2.5 ppm (C$\underline{H}_2$—CH$_2$—S, m, 2H)

Synthesis Example 6-2: Synthesis of Polymer F

[Chemical formula 24]

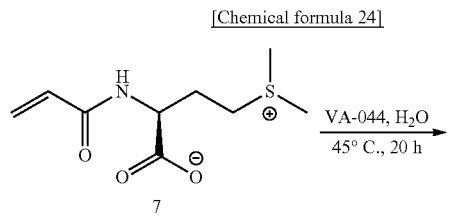

-continued

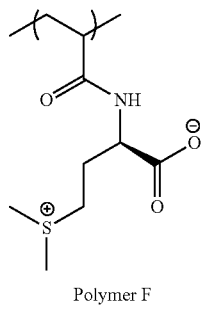

Polymer F

Monomer 7 (100 mg, 0.50 mmol) and azobis[2-(2-imidazoline-2-yl)propane]dihydrochloride (VA-044) (1.6 mg, 5.0 μmmol) were placed into a two-neck flask to be dissolved in H$_2$O (0.5 ml). Following 15 minutes of nitrogen bubbling, the temperature of the reaction system was raised to 45° C. to initiate polymerization. After 20 hours, the reaction solution was reprecipitated with 10 ml of acetone to give Polymer F.

Yield 100 mg $^1$H-NMR (D$_2$O, 400 MHz)

4.3-4.6 ppm (NH—C$\underline{H}$—COOH), 3.2-3.4 ppm (CH$_2$—C$\underline{H}_2$—S(CH$_3$)$_2$), 2.8-3.0 ppm (CH$_2$—S(C$\underline{H}_3$)$_2$), 1.4-2.4 ppm (C$\underline{H}_2$—CH$_2$—S, main chain of the polymer)

Similar to Example 1 above, the number-average molecular weight and the molecular weight distribution (weight-average molecular weight/number-average molecular weight) of Polymer F obtained were determined by gel permeation chromatography measurement using a differential refractometer as a detector. The number-average molecular weight and the molecular weight distribution of Polymer F were 4,900 and 2.53, respectively.

Example 7: Synthesis of Polymer G

Synthesis Example 7-1: Synthesis of Polymer 8

[Chemical formula 25]

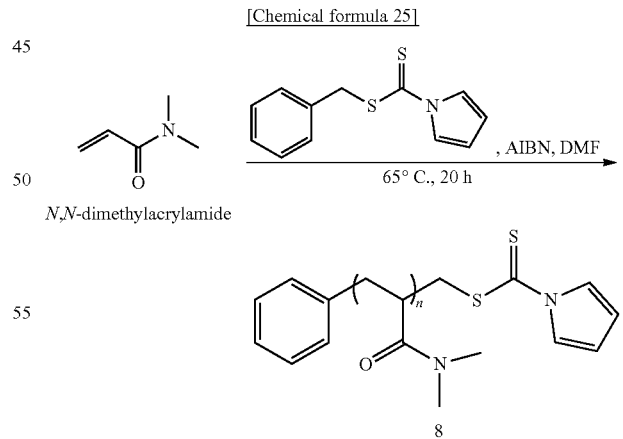

N,N-dimethylacrylamide (2.52 g, 25.4 mmol), benzyl 1H-pyrrole-1-carbodithioate (93.0 mg, 0.40 mmol) and azobisisobutyronitrile (32.8 mg, 0.20 mmol) were placed into a two-neck flask to be dissolved in DMF (12 ml). Following 15 minutes of nitrogen bubbling, the temperature of the reaction system was raised to 65° C. to initiate polymerization. After 1.5 hours, the reaction solution was reprecipitated with 200 ml of MTBE to give Polymer 8.

Yield 1.4 g $^1$H-NMR (CD$_3$CN. 400 MHz)

7.2-7.4 ppm (phenyl group, 5H), 6.4 ppm (pyrrole group, 2H), 2.3-3.0 ppm (CONH(CH$_3$)$_2$), 1.1-1.9 ppm (main chain of the polymer)

The number-average molecular weight and the molecular weight distribution (weight-average molecular weight/number-average molecular weight) of Polymer 8 obtained were determined by gel permeation chromatography measurement using a differential refractometer as a detector.

Instruments used were the same as Example 1 above. Two connected columns, namely, Mixed-D manufactured by Agilent (particle size 5 μm, column size 4.6 mm×25 cm) were used. 11.5 mM lithium bromide-containing dimethylformamide was used as the developing solvent. The measurement conditions were a flow rate of 0.6 ml/min, a column temperature of 40° C., a sample concentration of 0.2 mg/ml and a feeding amount of 70 μL. Polyethylene glycol was used as a standard. As a result of the gel permeation chromatography measurement, the number-average molecular weight and the molecular weight distribution of Polymer 8 were 5,300 and 1.11, respectively.

Synthesis Example 7-2: Synthesis of Polymer G ber-average molecular weight) of Polymer G obtained were determined in the same manner as Example 1. As a result of the gel permeation chromatography measurement, the number-average molecular weight and the molecular weight distribution of Polymer G were 8,300 and 1.20, respectively.

Example 8-1

(Preparation of Protein Stabilizer)

Polymer A synthesized in Example 1 was dissolved in a phosphate buffer (pH 7.4) to a concentration of 1 mass % to prepare a protein stabilizer solution.

(Preparation of Protein Solution)

Horseradish peroxidase was dissolved in a phosphate buffer (pH 7.4) to a concentration of 2 ug/ml to prepare a protein solution.

(Evaluation of Protein-Stabilizing Effect)

50 μl of the protein solution was added to 1 ml of the protein stabilizer solution to prepare a test solution. The test solution was stored at 4° C. After 2 and 5 days, 10 of the test solution was added to a 96-well plate, to which 100 μl of

[Chemical formula 26]

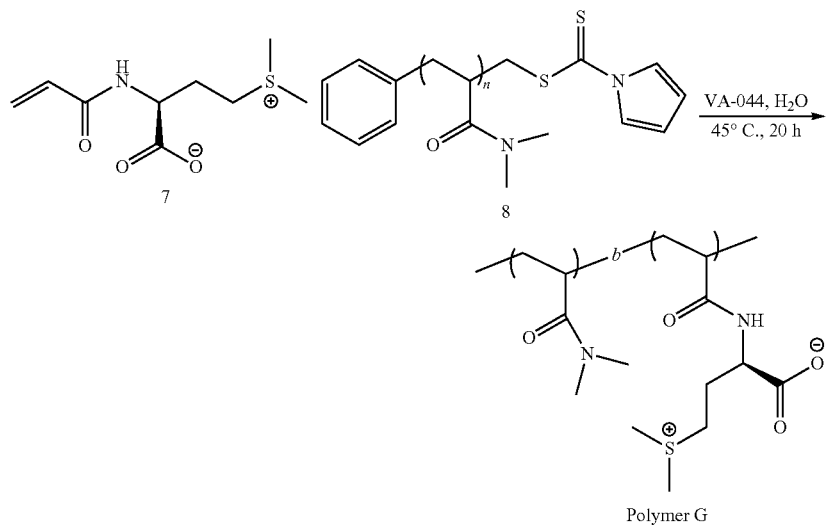

Polymer G

Monomer 7 (100 mg, 0.50 mmol), Polymer 8 (53 mg, 10.0 μmol) and azobis[2-(2-imidazoline-2-yl)propane]dihydrochloride (VA-044) (1.6 mg, 5.0 μmol) were placed into a two-neck flask to be dissolved in H$_2$O (0.5 ml). Following 15 minutes of nitrogen bubbling, the temperature of the reaction system was raised to 45° C. to initiate polymerization. After 20 hours, the reaction solution was reprecipitated with 10 ml of acetone to give Polymer G.

Yield 120 mg $^1$H-NMR (D$_2$O, 400 MHz)

4.3-4.6 ppm (NH—CH—COOH), 3.2-3.4 ppm (CH$_2$—CH$_2$—S(CH$_3$)$_2$), 2.8-3.0 ppm (CONH(CH$_3$)$_2$ (DMAAm), CH$_2$—S(CH$_3$)$_2$), 1.4-2.4 ppm (CH$_2$—CH$_2$—S, main chain of the polymer)

The number-average molecular weight and the molecular weight distribution (weight-average molecular weight/num- ABTS (2,2'-azobis(3-ethylbenzothiazoline-6-sulfonic acid) ammonium salt) solution (SeraCare Life Sciences) was added and the resultant was shaken at room temperature for 30 minutes. After shaking, 100 μl of a 1 mass % sodium dodecyl sulfate solution was added to terminate the reaction. Absorbance at 410 nm was determined to evaluate the protein-stabilizing effect.

Specifically, absorbance immediately after the preparation of the test solution and absorbance after 2 and 5 days of storing were determined to calculate the residual enzymatic activity (%) by the following equation (Equation 1). The protein-stabilizing effect was evaluated in terms of the residual enzymatic activity; where higher residual enzymatic activity indicates higher protein-stabilizing effect. The evaluation results are shown in Table 1.

Measurement instrument: Plate reader manufactured by DS Pharma Biomedical Co., Ltd.

Measurement conditions: Room temperature, 410 nm

[Equation 1]

$$\text{Residual enzymatic activity}(\%) = \frac{[\text{Absorbance of test solution after storing}]}{[\text{Absorbance of test solution immediately after preparation}]} \times 100 \quad \text{(Equation 1)}$$

Example 8-2

The protein-stabilizing effect was evaluated in the same manner as Example 8-1 except that Polymer B was used a protein stabilizer, which was dissolved in a phosphate buffer (pH 7.4) to concentrations of 1 mass % and 0.1 mass % to prepare protein stabilizer solutions. The evaluation results are shown in Table 1.

Example 9

(Evaluation of Freeze-Thaw Stabilizing Effect)

50 μl of the protein solution was added to 1 ml of each protein stabilizer solution described in Example 8-2 to prepare freeze-thaw stability test solutions. The freeze-thaw stability test solution was frozen at −78° C. and thawed at 4° C. for 3-10 times. Thereafter, 10 μl/well of the test solution was added to a 96-well plate, to which 100 μl of an ABTS (2,2'-azobis(3-ethylbenzothiazoline-6-sulfonic acid)ammonium salt) solution (SeraCare Life Sciences) was added and the resultant was shaken at room temperature for 30 minutes. After shaking, 100 μl of a 1 mass % sodium dodecyl sulfate solution was added to terminate the reaction. Absorbance at 410 nm was determined to evaluate the freeze-thaw stabilizing effect.

Specifically; absorbance immediately after the preparation of the freeze-thaw stability test solution and absorbance after 3-10 times of freeze-thaw were determined to calculate the residual enzymatic activity (%) by the following equation (Equation 2). The freeze-thaw stabilizing effect was evaluated in terms of the residual enzymatic activity, where higher residual enzymatic activity indicates higher freeze-thaw stabilizing effect.

The evaluation results are shown in Table 2.

Measurement instrument: Plate reader manufactured by DS Pharma Biomedical Co., Ltd.

Measurement conditions: Room temperature, 410 nm

[Equation 2]

$$\text{Residual enzymatic activity}(\%) = \frac{[\text{Absorbance of freeze-thaw stability test solution after freeze-thaw}]}{[\text{Absorbance of freeze-thaw stability test solution immediately after preparation}]} \times 100 \quad \text{(Equation 2)}$$

Example 10

(Preparation of Protein Stabilizer Solution)

Polymer B synthesized in Example 2 was dissolved in a 50 vol % aqueous ethanol solution to concentrations of 0.2, 0.1 and 0.05 mass % to prepare protein stabilizer solutions.

(Preparation of DPPH Solution)

DPPH (1,1-diphenyl-2-picrylhydrazyl) was dissolved in ethanol to a concentration of 0.25 mM to prepare a DPPH solution, (Evaluation of Antioxidant Property)

50 μl/well of the protein stabilizer solution at each concentration was added to a 96-well plate, to which 100 μl of 0.25M acetate buffer (pH 5.5) and 100 μl of the DPPH solution were added to prepare an antioxidant property test solution. After the prepared antioxidant property test solution was left to stand in the dark for 30 minutes, absorbance at 540 nm was determined. Blank solution 1 was prepared in the same manner as the preparation of the antioxidant property test solution except that 50 μl of a 50% aqueous ethanol solution was added instead of the protein stabilizer solution.

Blank solution 2 was prepared in the same manner as the preparation of the antioxidant property test solution except that 100 μl of ethanol was added instead of the DPPH solution.

Blank solution 3 was prepared in the same manner as the preparation of the antioxidant property test solution except that 50 μl of a 50% aqueous ethanol solution and 100 μl of ethanol were added instead of the protein stabilizer solution and the DPPH solution, respectively.

Subsequently, absorbance of the protein stabilizer solution and absorbance of Blank solutions 1, 2 and 3 were determined to calculate the DPPH radical scavenging rate (%) by the following equation (Equation 3). The antioxidant property was evaluated in terms of the DPPH radical scavenging rate, where higher DPPH radical scavenging rate indicates higher antioxidant property. The evaluation results are shown in Table 3.

Measurement instrument: Plate reader manufactured by DS Pharma Biomedical Co., Ltd.

Measurement conditions: Room temperature, 540 nm

[Equation 3]

$$\text{DPPH radical scavenging rate}(\%) = \frac{[(\text{Absorbance of Blank solution 1} - \text{Absorbance of Blank solution 3}) - (\text{Absorbance of protein stabilizer solution} - \text{Absorbance of Blank solution 2})]}{(\text{Absorbance of Blank solution 1} - \text{Absorbance of Blank solution 3})} \times 100 \quad \text{(Equation 3)}$$

Comparative Example 1-1

(Synthesis example 6-2 was Carried Out Using DMF as Polymerization Solvent at Polymerization Temperature of 70° C.)

Monomer 7 (100 mg, 0.50 mmol) and 4,4'-azobis(4-cyanovaleric acid) (1.6 mg, 5.0 μmol) were placed into a two-neck flask to be dissolved in DMF (0.5 mi). Following 15 minutes of nitrogen bubbling, the temperature of the reaction system was raised to 70° C. to initiate polymerization. After 20 hours, the reaction solution was reprecipitated with 10 ml of acetone but polymer was not Obtained.

Comparative Example 1-2

(Synthesis Example 6-2 was Carried Out at Polymerization Temperature of 70° C.)

Monomer 7 (100 mg, 0.50 mmol) and 4,4'-azobis(4-cyanovaleric acid) (1.6 mg, 5.0 μmol) were placed into a two-neck flask to be dissolved in $H_2O$ (0.5 ml). Following 15 minutes of nitrogen bubbling, the temperature of the reaction system was raised to 70° C. to initiate polymerization. After 20 hours, the reaction solution was reprecipitated with 10 ml of acetone but polymer was not obtained.

Comparative Example 2-1

A protein-stabilizing effect was evaluated in the same manner as Example 8-1 except that only a phosphate buffer (pH 7.4) and no protein stabilizer were used. The evaluation results are shown in Table 1.

Comparative Example 2-2

A protein-stabilizing effect was evaluated in the same manner as Example 84 except that DMSP was used as a protein stabilizer, which was dissolved in a phosphate buffer (pH=7.4) to a concentration of 0.1 mass % to prepare a protein stabilizer solution. The evaluation results are shown in Table 1.

Comparative Example 2-3

A protein-stabilizing effect was evaluated in the same manner as Example 8-1 except that polyethylene glycol (PEG) was used as a protein stabilizer, which was dissolved in a phosphate buffer (pH 7.4) to a concentration of 0.1 mass % to prepare a protein stabilizer solution. The evaluation results are shown in Table 1.

Comparative Example 2-4

A protein-stabilizing effect was evaluated in the same manner as Example 8-1 except that BSA (bovine serum albumin) was used as a protein stabilizer, which was dissolved in a phosphate buffer (pH=7.4) to a concentration of 0.1 mass % to prepare a protein stabilizer solution. The evaluation results are shown in Table 1.

As can be appreciated from Table 1, uses of Polymer A of Example 8-1 and Polymer B of Example 8-2 as protein stabilizers were shown to exhibit a significant protein-stabilizing effect as compared to the comparative examples.

Comparative Example 3-1

A freeze-thaw stabilizing effect was evaluated in the same manner as Example 9 except that only a phosphate buffer (pH 7.4) and no protein stabilizer were used. The evaluation results are shown in Table 2.

Comparative Example 3-2

A freeze-thaw stabilizing effect was evaluated in the same manner as Example 9 except that DMSP was used as a protein stabilizer, which was dissolved in a phosphate buffer (pH=7.4) to a concentration of 0.1 mass % to prepare a protein stabilizer solution. The evaluation results are shown in Table 2.

Comparative Example 3-3

A freeze-thaw stabilizing effect was evaluated in the same manner as Example 9 except that BSA (bovine serum albumin) was used as a protein stabilizer, which was dissolved in a phosphate buffer (pH=7.4) to a concentration of 0.1 mass % to prepare a protein stabilizer solution. The evaluation results are shown in Table 2.

As can be appreciated from Table 2, use of Polymer B as a protein stabilizer was shown to exhibit a significant freeze-thaw stabilizing effect as compared to the comparative examples.

Comparative Example 4-1

An antioxidant property was evaluated in the same manner as Example 10 except that DMSP was used as an antioxidant, which was dissolved in a 50% aqueous ethanol solution to concentrations of 0.2, 0.1 and 0.05 mass % to prepare antioxidant solutions. The evaluation results are shown in Table 3.

Comparative Example 4-2

An antioxidant property was evaluated in the same manner as Example 10 except that PEG (molecular weight: 4000) was used as an antioxidant, which was dissolved in a 50% aqueous ethanol solution to concentrations of 0.2, 0.1 and 0.05 mass %© to prepare antioxidant solutions. The evaluation results are shown in Table 3.

As can be appreciated from Table 3, use of Polymer B as a protein stabilizer was shown to exhibit a significant antioxidant property as compared to the comparative examples.

Accordingly, Polymer B that has a zwitterion effective in enhancing stability of a protein serves as a high-molecular protein stabilizer effective in stabilizing the protein in a small amount. At the same time, it was also confirmed to be a zwitterionic polymer having an antioxidant property.

Example 11: Synthesis of Polymer H

Synthesis Example 8-1: Synthesis of Polymer 9

[Chemical formula 27]

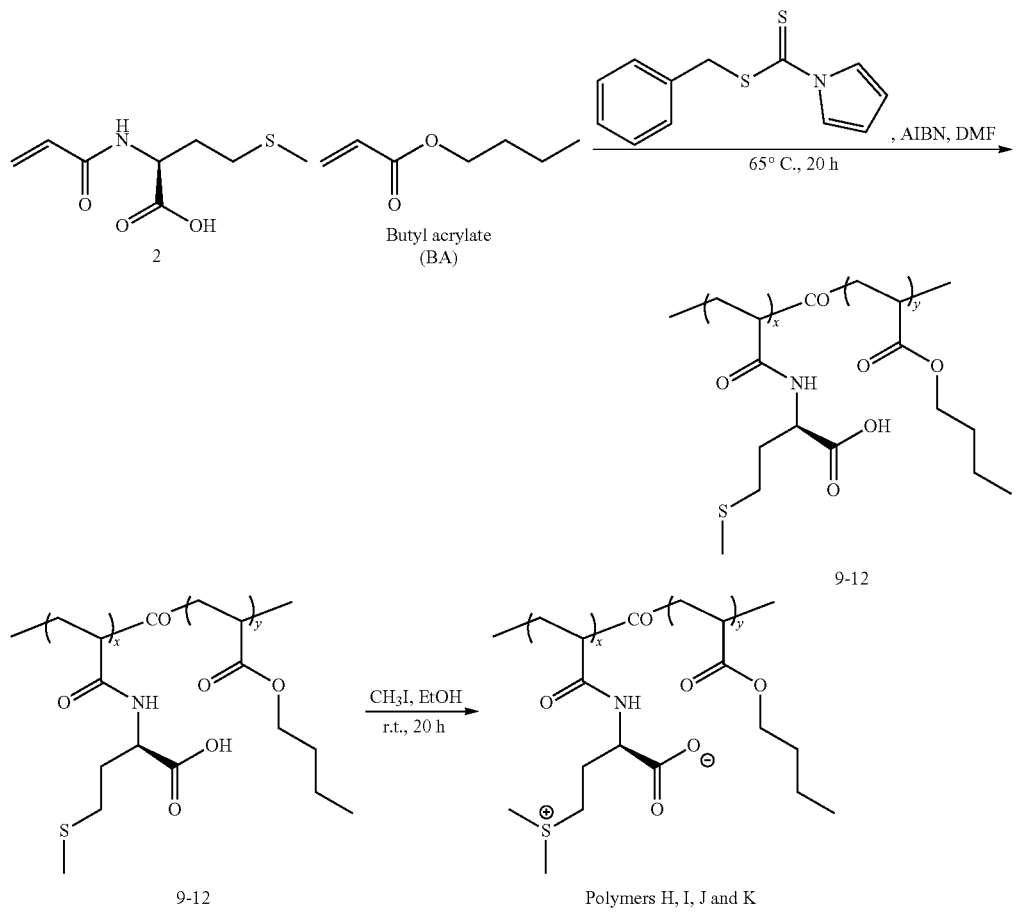

Monomer 2 (1.8 g, 9.0 mmol), butyl acrylate (128 mg, 1.0 mmol), benzyl 1 LI-pyrrole-1-carbodithioate (46.6 mg, 0.20 mmol) and azobisisobutyronitrile (16.4 mg, 0.10 mmol) were placed into a two-neck flask to be dissolved in ethanol (1 ml). Following 15 minutes of nitrogen bubbling, the temperature of the reaction system was raised to 65° C. to initiate polymerization. After 20 hours, the reaction solution was reprecipitated with 200 ml of MTBE/Hexane mixed solvent to give Polymer 9.
Composition ratio (mole ratio) x:y=86:14
Yield 1.8 g Synthesis Example 8-2: Synthesis of Polymer H Polymer 9 (1.00 g) was placed into an eggplant-shaped flask to be dissolved in 10 ml of ethanol. 2 mL of iodomethane was added to the reaction solution and the resultant was agitated at room temperature for 20 hours. The solvent was distilled away under reduced pressure to give Polymer H.
Yield 1.8 g
The number-average molecular weight and the molecular weight distribution (weight-average molecular weight/number-average molecular weight) of Polymer H obtained were determined in the same manner as Example 1 above.

The number-average molecular weight and the molecular weight distribution of Polymer H were 8,300 and 1.31, respectively.

Example 12: Synthesis of Polymer I

Synthesis Example 9-1: Synthesis of Polymer 10

Polymer 10 was obtained in the same manner as Synthesis example 8-1 except that Monomer 2. (1.4 g, 7.0 mmol) and butyl acrylate (384 mg, 3.0 (nmol) were used.
Composition ratio (mole ratio) x:y=68:32
Yield 1.7 g Synthesis Example 9-2: Synthesis of Polymer I Polymer I was obtained from Polymer 10 in the same manner as Synthesis example 8-2.
Yield 1.8 g
The number-average molecular weight and the molecular weight distribution (weight-average molecular weight/number-average molecular weight) of Polymer I obtained were determined in the same manner as Example 4 above.

The number-average molecular weight and the molecular weight distribution of Polymer I were 13,200 and 1.08, respectively.

Example 13: Synthesis of Polymer J

Synthesis Example 10-1: Synthesis of Polymer 11

Polymer 11 was obtained in the same manner as Synthesis example 8-1 except that Monomer 2 (1.0 g, 5.0 mmol) and butyl acrylate (640 mg, 5.0 mmol) were used.
Composition ratio (mole ratio) x:y=50:50
Yield 1.6 g Synthesis Example 10-2: Synthesis of Polymer J Polymer J was obtained from Polymer 11 in the same manner as Synthesis example 8-2.
Yield 1.7 g
The number-average molecular weight and the molecular weight distribution (weight-average molecular weight/number-average molecular weight) of Polymer J obtained were determined in the same manner as Example 4 above.
The number-average molecular weight and the molecular weight distribution of Polymer J were 14,000 and 1.10, respectively.

Example 14: Synthesis of Polymer K

Synthesis Example 11-1: Synthesis of Polymer 12

Polymer 12 was obtained in the same manner as Synthesis example 8-1 except that Monomer 2 (0.6 g, 3.0 mmol) and butyl acrylate (896 mg, 7.0 mmol) were used.
Composition ratio (mole ratio) x:y=32:68
Yield 1.4 g Synthesis Example 11-2: Synthesis of Polymer K Polymer K was obtained from Polymer 12 in the same manner as Synthesis example 8-2.
Yield 1.5 g
The number-average molecular weight and the molecular weight distribution (weight-average molecular weight/number-average molecular weight) of Polymer K obtained were determined in the same manner as Example 4 above.
The number-average molecular weight and the molecular weight distribution of Polymer J were 13,000 and 1.16, respectively.
Here, the mole ratios of zwitterionic structural unit x and structural unit y in Polymers 9-12 as well as Polymers J and K obtained in Examples 11-14 were as shown in Table 5 below.

Examples 15

Example 15-1

The protein-stabilizing effect of Polymer B was evaluated in the same manner as Example 8-2 except that it was stored at 4° C. for 13, 28 and 62 days. The evaluation results are shown in Table 4.

Example 15-2

A protein stabilizer solution was prepared in the same manner as Example 15-1 above except that Polymer H was used as the protein stabilizer instead of Polymer B. The evaluation results are shown in Table 4.

Example 15-3

A protein stabilizer solution was prepared in the same manner as Example 15-1 above except that Polymer I was used as the protein stabilizer instead of Polymer B. The evaluation results are shown in Table 4.

Example 15-4

A protein stabilizer solution was prepared in the same manner as Example 15-1 above except that Polymer J was used as the protein stabilizer instead of Polymer B. The evaluation results are shown in Table 4.

Example 15-5

A protein stabilizer solution was prepared in the same manner as Example 15-1 above except that Polymer K was used as the protein stabilizer instead of Polymer B. The evaluation results are shown in Table 4.

Comparative Example 5

A protein stabilizer solution was prepared in the same manner as Example 15-1 above except that only a phosphate buffer (pH 7.4) and no protein stabilizer were used. The evaluation results are shown in Table 4.

As can be appreciated from Table 4, a protein-stabilizing effect can be achieved for a long period of time by copolymerizing with butyl acrylate.

TABLE 1

| | Protein stabilizer | | Residual enzymatic activity (%) | | |
|---|---|---|---|---|---|
| | Name | Concentration (mass %) | Beginning | After 2 days | After 5 days |
| Example 8-1 | Polymer A | 1 | 100 | 94 | 91 |
| Example 8-2 | Polymer B | 1 | 100 | 95 | 93 |
| | | 0.1 | 100 | 100 | 93 |
| Comparative example 2-1 | — | — | 100 | 20 | 0 |
| Comparative example 2-2 | DMSP | 0.1 | 100 | 20 | 0 |
| Comparative example 2-3 | PEG | 0.1 | 100 | 77 | 75 |
| Comparative example 2-4 | BSA | 1 | 100 | 80 | 89 |

TABLE 2

| | Protein stabilizer | | Residual enzymatic activity (%) | | |
|---|---|---|---|---|---|
| | Name | Concentration (mass %) | Beginning | 3 times | 10 times |
| Example 9 | Polymer B | 1 | 100 | 99 | 99 |
| | | 0.1 | 100 | 99 | 95 |
| Comparative example 3-1 | — | — | 100 | 25 | 0 |
| Comparative example 3-2 | DMSP | 0.1 | 100 | 38 | 12 |
| Comparative example 3-3 | BSA | 1 | 109 | 99 | 95 |

TABLE 3

| | Protein stabilizer | | DPPH radical |
| --- | --- | --- | --- |
| | Name | Concentration (mass %) | scavenging rate (%) |
| Example 10 | Polymer B | 0.2 | 65 |
| | | 0.1 | 39 |
| | | 0.05 | 36 |
| Comparative example 4-1 | DMSP | 0.2 | 41 |
| | | 0.1 | 20 |
| | | 0.05 | 2 |
| Comparative example 4-2 | PEG | 0.2 | 19 |
| | | 0.1 | 10 |
| | | 0.05 | 0 |

TABLE 4

| | Protein stabilizer | | Residual enzymatic activity (%) | | | |
| --- | --- | --- | --- | --- | --- | --- |
| | Name | Concentration (mass %) | Beginning | After 13 days | After 28 days | After 62 days |
| Example 8-2 | Polymer B | 0.1 | 100 | 83 | 79 | 58 |
| Example 15-1 | Polymer H | 0.1 | 100 | 100 | 100 | 80 |
| Example 15-2 | Polymer I | 0.1 | 100 | 100 | 100 | 83 |
| Example 15-3 | Polymer J | 0.1 | 100 | 100 | 100 | 81 |
| Example 15-4 | Polymer K | 0.1 | 100 | 100 | 100 | 85 |
| Comparative example 5 | — | — | 100 | 5 | 0 | 0 |

TABLE 5

| Polymers 9-12 | Polymers H-K | Zwitterionic repeating unit x: BA-derived repeating unit y (Mole ratio) |
| --- | --- | --- |
| 9 | H | 86:14 |
| 10 | I | 68:32 |
| 11 | J | 50:50 |
| 12 | K | 32:68 |

INDUSTRIAL APPLICABILITY

As described above, the present invention can provide a high-molecular protein stabilizer having a zwitterion effective in enhancing stability of a protein, which is effective in stabilizing the protein in a small amount. Furthermore, since the zwitterionic polymer of the present invention has a stabilizing effect and an antioxidant property at the same time, it can also enhance an antioxidant property of the high-molecular protein stabilizer. The protein stabilizer containing the zwitterionic polymer of the present invention can especially, enhance stability of a protein stored at a low temperature, for example, 4° C., for a long period of time and stability of a protein upon a freeze-thaw process.

The invention claimed is:

1. A zwitterionic polymer comprising a repeating unit represented by Formula (1) below and having a number-average molecular weight of 1,000-1,000,000,

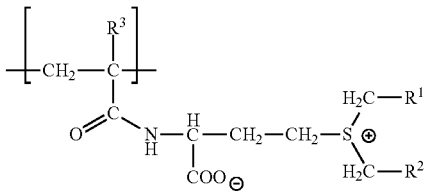

(1)

wherein $R^1$ and $R^2$ is each independently selected from a hydrogen atom, a linear, branched or cyclic C1-C6 alkyl group, a C6-C20 aromatic group or a C1-C6 alkylene group in which $R^1$ and $R^2$ are linked to each other, and $R^3$ represents a hydrogen atom or a methyl group.

2. The zwitterionic polymer according to claim 1, wherein $R^1$ and $R^2$ in Formula (1) are both hydrogen atoms.

3. The zwitterionic polymer according to claim 1, further comprising a structural unit derived from (meth)acrylate ester, wherein the ratio of the mole number x of the repeating unit represented by Formula (1) above and the mole number y of the structural unit derived from (meth)acrylate ester is in a range of x:y=10:90-95:5.

4. A method for producing the zwitterionic polymer according to claim 1, the method comprising A) and B) below in this order:
A) radically polymerizing a sulfide acrylamide monomer represented by Formula (2) below;

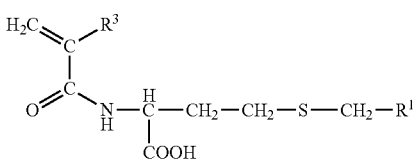

(2)

wherein $R^1$ represents a hydrogen atom, a linear, branched or cyclic C1-C6 alkyl group or a C6-C20 aromatic group, and $R^3$ represents a hydrogen atom or a methyl group); and
B) allowing the polymer obtained in A) above to react with a sulfide-reactive compound represented by Formula (3) below, $$X—CH_2—R^2 \quad (3)$$

wherein X represents a chlorine atom, a bromine atom, an iodine atom, a mesyl group (methanesulfonyl group), a tosyl group (p-toluenesulfonyl group) or a trifluoromethanesulfonyl group, and $R^2$ represents a hydrogen atom, a linear, branched or cyclic C1-C6 alkyl group or a C6-C20 aromatic group).

5. A method for producing the zwitterionic polymer according to claim 1, comprising
radically polymerizing a zwitterionic monomer represented by Formula (4) below in an aqueous solvent at 60° C. or lower,

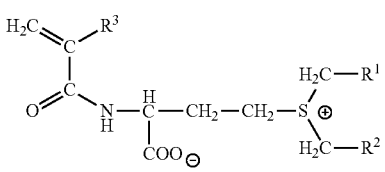

(4)

wherein $R^1$ and $R^2$ each independently represents a hydrogen atom, a linear, branched or cyclic C1-C6 alkyl group, a C6-C20 aromatic group or a C1-C6 alkylene group in which $R^1$ and $R^2$ are linked to each other, and $R^3$ represents a hydrogen atom or a methyl group.

6. A zwitterionic monomer represented by Formula (4) below,

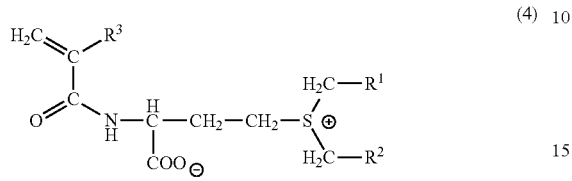

(4)

wherein $R^1$ and $R^2$ each independently represents a hydrogen atom, a linear, branched or cyclic C1-C6 alkyl group, a C6-C20 aromatic group or a C1-C6 alkylene group in which $R^1$ and $R^2$ are linked to each other, and $R^3$ represents a hydrogen atom or a methyl group.

7. A protein stabilizer comprising the zwitterionic polymer according to claim 1.

8. A protein stabilizer comprising the zwitterionic polymer according to claim 2.

9. A protein stabilizer comprising the zwitterionic polymer according to claim 3.

* * * * *